US012778894B2

United States Patent
(12) United States Patent
Vilhelmsen et al.

(10) Patent No.: US 12,778,894 B2
(45) Date of Patent: Nov. 3, 2026

(54) TABLET COMPRISING A SALT OF N-(8-(2-HYDROXYBENZOYL)AMINO) CAPRYLIC ACID

(71) Applicant: Novo Nordisk A/S, Bagsvaerd (DK)

(72) Inventors: Thomas Kvistgaard Vilhelmsen, Solroed Strand (DK); Isabell Vargas Damgaard, Frederiksberg (DK)

(73) Assignee: Novo Nordisk A/S, Bagsvaerd (DK)

( * ) Notice: Subject to any disclaimer, the term of this patent is extended or adjusted under 35 U.S.C. 154(b) by 232 days.

(21) Appl. No.: 18/577,720

(22) PCT Filed: Jul. 14, 2022

(86) PCT No.: PCT/EP2022/069704
§ 371 (c)(1),
(2) Date: Jan. 9, 2024

(87) PCT Pub. No.: WO2023/285580
PCT Pub. Date: Jan. 19, 2023

(65) Prior Publication Data
US 2024/0335388 A1 Oct. 10, 2024

(30) Foreign Application Priority Data
Jul. 15, 2021 (EP) .................................... 21185861

(51) Int. Cl.

| | |
|---|---|
| ***A61K 9/20*** | (2006.01) |
| ***A61K 38/00*** | (2006.01) |
| ***A61K 38/26*** | (2006.01) |
| ***A61P 3/04*** | (2006.01) |
| ***A61P 3/10*** | (2006.01) |

(52) U.S. Cl.
CPC .......... *A61K 9/2013* (2013.01); *A61K 9/2077* (2013.01); *A61K 38/26* (2013.01)

(58) Field of Classification Search
None
See application file for complete search history.

(56) References Cited

U.S. PATENT DOCUMENTS

| | | | |
|---|---|---|---|
| 8,541,024 B2 | 9/2013 | Ono et al. | |
| 8,911,779 B2 | 12/2014 | Kitajima et al. | |
| 10,335,369 B2 | 7/2019 | Vilhelmsen | |
| 10,933,120 B2 | 3/2021 | Vilhelmsen et al. | |
| 2012/0034301 A1* | 2/2012 | Kitajima .............. | A61K 9/2077 424/464 |

(Continued)

FOREIGN PATENT DOCUMENTS

| | | |
|---|---|---|
| CN | 107812181 A | 3/2018 |
| CN | 111683676 A | 9/2020 |

(Continued)

OTHER PUBLICATIONS

American Pharmacists Association, "Tablet Design", Tableting Specification Manual, 2006, 7th Edition, pp. 51-57, 68, 72, 73.

(Continued)

*Primary Examiner* — Kyung S Chang
(74) *Attorney, Agent, or Firm* — Leon Y. Lum

(57) ABSTRACT

The invention relates to a tablet comprising a salt of N-(8-(2-hydroxy benzoyl)amino)caprylic acid. The invention further relates to processes for the preparation such a tablet, and its use in medicine.

14 Claims, 11 Drawing Sheets

1

(56) References Cited

U.S. PATENT DOCUMENTS

| | | | |
|---|---|---|---|
| 2016/0263039 A1 | 9/2016 | Tanabe et al. | |
| 2019/0008761 A1 | 1/2019 | Alevizache | |
| 2020/0000728 A1 | 1/2020 | Pedersen et al. | |
| 2020/0113842 A1 | 4/2020 | Sekine | |

FOREIGN PATENT DOCUMENTS

| | | | |
|---|---|---|---|
| EP | 1905430 | A1 | 4/2008 |
| EP | 3646856 | A1 | 5/2020 |
| JP | 6356660 | B2 | 7/2018 |
| WO | 9630036 | A1 | 10/1996 |
| WO | 0046182 | A1 | 8/2000 |
| WO | 0192206 | A1 | 12/2001 |
| WO | 2003080023 | A2 | 10/2003 |
| WO | 2006097537 | | 9/2006 |
| WO | 2007121318 | A2 | 10/2007 |
| WO | 2008028859 | A1 | 3/2008 |
| WO | 2010020978 | A1 | 2/2010 |
| WO | 2012080471 | A1 | 6/2012 |
| WO | 2013139694 | A1 | 9/2013 |
| WO | 2013139695 | A1 | 9/2013 |
| WO | 2013187395 | A1 | 12/2013 |
| WO | 2013189988 | A1 | 12/2013 |
| WO | 2014177683 | A1 | 11/2014 |
| WO | 2015087561 | A1 | 6/2015 |
| WO | 2017047586 | A1 | 3/2017 |
| WO | 2019215063 | A1 | 11/2019 |
| WO | 2021023855 | A1 | 2/2021 |
| WO | 2021043803 | A1 | 3/2021 |

OTHER PUBLICATIONS

American Pharmacists Association, "Guidelines for Using This Manual," Tableting Specification Manual, 2006, 7th Edition, pp. 1-8.

Ashland's Film Coating Troubleshooting Guide, "Tablet Breakage", 2019, 5 pages, accessed Dec. 17, 2021, http://filmcoating-troubleshooting.com/film_coating/tablet-breakage.html.

* cited by examiner

TABLET COMPRISING A SALT OF N-(8-(2-HYDROXYBENZOYL)AMINO)CAPRYLIC ACID

CROSS-REFERENCE TO RELATED APPLICATIONS

This application is a 35 U.S.C. § 371 National Stage application of International Application PCT/EP2022/069704 (WO2023/285580), filed Jul. 14, 2022, which claims priority to European Patent Application 21185861.8, filed Jul. 15, 2021; the contents of which are incorporated herein by reference.

The invention relates to a tablet comprising a salt of N-(8-(2-hydroxybenzoyl)amino)caprylic acid, its medical use as well as to a method of producing a tablet comprising a salt of N-(8-(2-hydroxybenzoyl)amino)caprylic acid.

BACKGROUND

About 70% of all medication is administered as tablets. Yet, injections are the most common means for administering protein and peptide drugs. Patient compliance with drug administration regimens by any of these parenteral routes is generally poor and severely restricts the therapeutic value of the drug, particularly for diseases such as diabetes.

Oral administration presents a series of attractive advantages over injection. These advantages are particularly relevant for the treatment of paediatric patients and include the avoidance of pain and discomfort associated with injections and the elimination of possible infections caused by inappropriate use or reuse of needles. Moreover, oral formulations are less expensive to produce, because they do not need to be manufactured under sterile conditions. However, poor bioavailability of proteins and peptides makes the development of oral dosage forms comprising peptides challenging.

N-(8-(2-hydroxybenzoyl)amino)caprylates such as sodium N-(8-(2-hydroxybenzoyl)amino)caprylate have been found to increase oral bioavailability of GLP-1 analogues as described in e.g. WO 2010/020978, WO 2012/080471, WO 2013/189988, WO 2013/139694, WO 2013/139695 and WO 2014/177683.

Despite these findings, there is still a need to further optimise oral dosage forms comprising a salt of N-(8-(2-hydroxybenzoyl)amino)caprylic acid and a GLP-1 peptide.

Tablets are solid formulations having a certain shape and are a widely used dosage form in pharmaceutical products. Tablets are often manufactured by powder compaction to be a certain shape (called "tableting"). A tablet typically comprises a body and two opposing cups. Based on the shape of the body of the tablet, tablets are often broadly categorised as either "rounds" or "shapes". The tableting specification manual of the American Pharmacists Association ($7^{th}$ edition) describes the general terminology with respect to tablet design. For instance, a round tablet has a configuration in which all axes are equal from the centre point of the tip face. Round tablets have a substantially circular body and have a minor and major axis that are of substantially the same length. Shaped tablets include the following configuration according to the tableting specification manual of the American Pharmacists Association ($7^{th}$ edition): capsule, modified capsule, oval and geometric shapes. Examples of shaped tablets are oval tablets and capsule shaped tablets. Oval or oval-shaped tablets have a body comprising an end radius, a side radius, a core height, a major and a minor axis, where the ratio between the major and the minor axis is above 1.0. Capsule tablets or capsule-shaped tablets have a body comprising an end radius, a core height, and a major and a minor axis, where the ratio between the major and the minor axis is above 1.0.

In addition to different shapes of the tablet body, a tablet may also be defined by the shape of the tablet cup. For instance, a convex oval tablet, is an oval-shaped tablet having at least one convex cup. In the industry, the term concave is used to describe both the concave surface of a punch cup and the surface of the produced tablet. Technically, the punch cup is usually a concavity and therefore produces a tablet with a convex cup. There are two commonly cup designs: standard cup and compound cup. A compound cup design is one in which at least two arcs or radii are generated from the cup's centre point across the cup's diameter, minor axis or major axis. A standard cup design is one in which a single arc is generated from the cup's centre point across the cup's diameter, minor axis or major axis.

An underestimated factor, which however plays a vital role in patient compliance, is the organoleptic aspect of a tablet. The organoleptic properties of a tablet basically determine the willingness of a patient to swallow a tablet. For instance, certain shapes have better organoleptic properties than others, because they appear to be easier to swallow. Also, or alternatively, tablets having distinct defects and flaws in or on their surface may be perceived as faulty and close to falling apart by consumers/patients, which leads to consumers rejecting such tablets and failure to comply with their medication scheme.

Thus, a major problem that can occur during or after tablet manufacture is cracking. This can manifest itself in a number of ways. It can range from surface cracking through to capping and lamination. Even though certain tablet shapes are generally less prone to the formation of cracks or other flaws on the tablet surface, such shapes are not always suitable for a given pharmaceutical composition and hence other solutions have to be found.

Thus, it is an object of the present disclosure to provide a tablet comprising a salt of N-(8-(2-hydroxybenzoyl)amino)caprylic acid which has good organoleptic properties. It is a further object that the tablet design is optimised such that the occurrence of cracks on the surface of the tablet are reduced during manufacturing.

DISCLOSURE OF THE INVENTION

The present invention relates to a tablet comprising a salt of N-(8-(2-hydroxybenzoyl)amino)caprylic acid such as sodium N-(8-(2-hydroxybenzoyl)amino)caprylate (SNAC). The tablet according to the invention is elongated. The tablet according to the invention has two compound cups and may have an oval-shaped or capsule-shaped body. The present invention is based on the realisation that when a pharmaceutical composition comprising a salt of N-(8-(2-hydroxybenzoyl)amino)caprylic acid such as sodium N-(8-(2-hydroxybenzoyl)amino)caprylate (SNAC) is compressed into a tablet, such as an oval-shaped tablet, one or more irregular crack(s) may form on or across the tablet cup more or less straight along and/or parallel to the major axis of the tablet upon tablet ejection.

The inventors have surprisingly found that it is advantageous to have a cup design, viewed from the front, where the central part of the cup is flattened while a rapid increase in cup depth at the periphery of the cup is maintained. Put differently, the inventors have surprisingly found that the formation of cracks during the tabletting process is drastically reduced when the index value is 0.67 or below. In addition, the inventors have found that a tablet height to width ratio of 0.9 or below, a tablet height to cup depth ratio of above 4.3, and a minor major radius to width ratio of above 1.15 can lead to good organoleptic properties.

In the disclosure of the present invention, embodiments and aspects will be described which will address the above object or which will address objects apparent from the below disclosure as well as from the description of exemplary embodiments.

Thus, in a first aspect, the invention relates to a tablet such as an elongated, oval-shaped compound cup tablet, comprising a salt of N-(8-(2-hydroxybenzoyl)amino)caprylic acid in a total amount of about 60 to 99.8% in weight based on the total weight of the tablet, the tablet having (a) a tablet height to width ratio of 0.9 or below, such as of about 0.05-0.9;
(b) a tablet height to cup depth ratio of above 4.3, such as of about 4.4-100;
(c) a minor major radius to width ratio of above 1.15, such as of about 1.16-100; and/or
(d) an index value of 0.67 or below, such as of about 0.05-0.67.

The salt of N-(8-(2-hydroxybenzoyl)amino)caprylic acid may be sodium N-(8-(2-hydroxybenzoyl)amino)caprylate (SNAC). The salt of N-(8-(2-hydroxybenzoyl)amino) caprylic acid such as SNAC may be granulated.

The tablet according to the first aspect may further comprise an active pharmaceutical ingredient such as a peptide. In some embodiments, the peptide may be a GLP-1 agonist. The GLP-1 agonist may be semaglutide. In some embodiments, the peptide may be present in a total amount of about 0.1 to 40% in weight based on the total weight of the tablet.

In some embodiments, the tablet may further comprise a lubricant. The lubricant may be present in a total amount of about 0.1-7% in weight based on the total weight of the tablet. The lubricant may be magnesium stearate.

In some embodiments, the tablet may further comprise one or more pharmaceutically acceptable excipient.

In a second aspect, there is provided a process for preparing a tablet according to the first aspect.

In a third aspect, there is provided a punch set comprising an upper punch, a lower punch, and a die for making a tablet according to the first aspect.

In a fourth aspect, there is provided a tablet according to the first aspect of the invention for use in medicine.

In an alternative fourth aspect, there is provided a method for treatment of diabetes or obesity comprising administering a tablet according to first aspect to a patient in need thereof. In some embodiments, the tablet is administered orally. In some embodiments, the tablet is administered once daily or less frequent such as once weekly.

In a fifth aspect, there is provided a tablet according to the first aspect of the invention for use in the treatment of diabetes or obesity.

BRIEF DESCRIPTION OF DRAWINGS

In the following, embodiments of the invention will be described with reference to the drawings, wherein.

The figures are schematic and simplified for clarity, and they just show details, which are essential to the understanding of the invention, while other details are left out. Throughout, the same reference numerals are used for identical or corresponding parts.

DESCRIPTION

Figure 1:
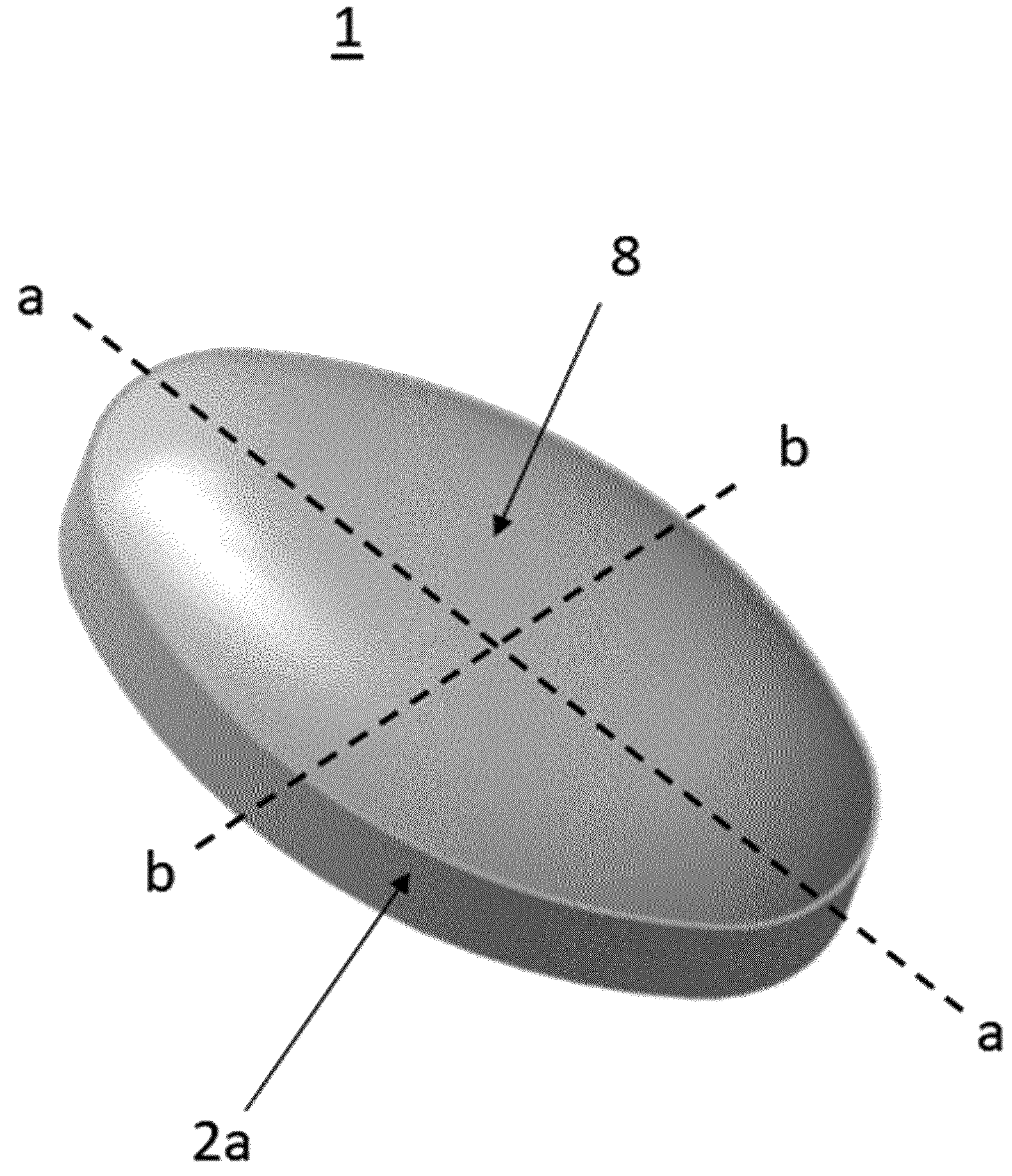
FIG. 1 is a top view of a tablet 1 according to the present invention

When in the following terms like “upper” and “lower”, “right” and “left”, “horizontal” and “vertical”, “clockwise” and “counter clockwise”, “front”, “end”, and “side” or similar relative expressions are used, these only refer to the appended figures and not to an actual situation of use. The shown figures are schematic representations for which reason the configuration of the different structures as well as their relative dimensions are intended to serve illustrative purposes only.

In the present specification, the use of the singular includes the plural, and the words “a”, “an” and “the” means “at least one”, unless specifically stated otherwise. Furthermore, the use of the term “including”, as well as other forms such as “includes” and “included”, is not limiting. As used herein, the conjunction “and” is intended to be inclusive and the conjunction “or” is not intended to be exclusive, unless otherwise indicated. For example, the phrase “or, alternatively” is intended to be exclusive. As used herein, the term “and/or” refers to any combination of the foregoing features including using a single feature.

Detailed descriptions are given below to specific embodiments of the present invention with reference to the drawing.

According to a first aspect, there is provided tablet 1 comprising a salt of N-(8-(2-hydroxybenzoyl)amino) caprylic acid in a total amount of about 60 to 99.8% in weight based on the total weight of the tablet, the tablet having (a) a tablet height to width ratio of 0.9 or below, such as of about 0.05-0.9;
(b) a tablet height to cup depth ratio of above 4.3, such as of about 4.4-100;
(c) a minor major radius to width ratio of above 1.15, such as of about 1.16-100; and/or
(d) an index value of 0.67 or below, such as of about 0.05-0.67.

The tablet 1 according to the first aspect of the invention is elongated and may also be referred to as an oval-shaped or a capsule-shaped compound cup tablet.

The tablet 1 may have an identification such as an engraving. In some embodiments, the tablet according to the invention is a debossed tablet. In some embodiments, the tablet according to the invention is an embossed tablet.

The total amount of the salt of N-(8-(2-hydroxybenzoyl)amino)caprylic acid may be about 65 to 99% in weight based on the total weight of the tablet. In some embodiments, the total amount of the salt of N-(8-(2-hydroxybenzoyl)amino)caprylic acid may be about 70 to 99% in weight based on the total weight of the tablet. In some embodiments, the total amount of the salt of N-(8-(2-hydroxybenzoyl)amino)caprylic acid may be about 75 to 99% in weight based on the total weight of the tablet. In some embodiments, the total amount of the salt of N-(8-(2-hydroxybenzoyl)amino)caprylic acid may be about 80 to 99% in weight based on the total weight of the tablet. In some embodiments, the total amount of the salt of N-(8-(2-hydroxybenzoyl)amino)caprylic acid may be about 85 to 99% in weight based on the total weight of the tablet. In some embodiments, the total amount of the salt of N-(8-(2-hydroxybenzoyl)amino)caprylic acid may be about 90 to 99% in weight based on the total weight of the tablet. In some embodiments, the total amount of the salt of N-(8-(2-hydroxybenzoyl)amino)caprylic acid may be about 70 to 98% in weight based on the total weight of the tablet. In some embodiments, the total amount of the salt of N-(8-(2-hydroxybenzoyl)amino)caprylic acid may be about 75 to 98% in weight based on the total weight of the tablet. In some embodiments, the total amount of the salt of N-(8-(2-hydroxybenzoyl)amino)caprylic acid may be about 80 to 98% in weight based on the total weight of the tablet. In some embodiments, the total amount of the salt of N-(8-(2-hydroxybenzoyl)amino)caprylic acid may be about 85 to 98% in weight based on the total weight of the tablet. In some embodiments, the total amount of the salt of N-(8-(2-hydroxybenzoyl)amino)caprylic acid may be about 90 to 98% in weight based on the total weight of the tablet. In some embodiments, the total amount of the salt of N-(8-(2-hydroxybenzoyl)amino)caprylic acid may be about 85 to 97% in weight based on the total weight of the tablet. In some embodiments, the total amount of the salt of N-(8-(2-hydroxybenzoyl)amino)caprylic acid may be about 90 to 97% in weight based on the total weight of the tablet. In some embodiments, the total amount of the salt of N-(8-(2-hydroxybenzoyl)amino)caprylic acid may be about 79 to 90% in weight based on the total weight of the tablet.

The salt of N-(8-(2-hydroxybenzoyl)amino)caprylic acid may be granulated.

In some embodiments, the salt of N-(8-(2-hydroxybenzoyl)amino)caprylic acid is sodium N-(8-(2-hydroxybenzoyl)amino)caprylate (SNAC), such as granulated SNAC.

The total weight of the tablet 1 may be about 50-1200 mg, such as about 100 mg or about 300 mg or about 500 mg or about 700 mg or about 1050 mg.

In some embodiments, the total weight of the tablet 1 is about 90-190 mg, such as about 100-175 mg. In some embodiments, the total weight of the tablet 1 is about 190-290 mg, such as about 200-280 mg. In some embodiments, the total weight of the tablet 1 is about 290-390 mg, such as about 300-380 mg. In some embodiments, the total weight of the tablet 1 is about 390-490 mg, such as about 400-485 mg. In some embodiments, the total weight of the tablet 1 is about 490-590 mg, such as about 500-585 mg. In some embodiments, the total weight of the tablet 1 is about 590-850 mg, such as about 600-830 mg. In some embodiments, the total weight of the tablet 1 is about 850-1200 mg, such as about 860-1150 mg.

The tablet 1 according to the first aspect, may further comprise an active pharmaceutical ingredient (API) such as a peptide and optionally a lubricant.

The active pharmaceutical ingredient may be present in a total amount of about 0.1 to 40% in weight based on the total weight of the tablet. In some embodiments the API is a peptide. In some embodiments, the peptide is a GLP-1 agonist. In some embodiments, the API is semaglutide.

The lubricant such as magnesium stearate may be present in a total amount of about 0.1-7%, such as 0.5-3% in weight based on the total weight of the tablet. In some embodiments, the lubricant is present in a total amount of about 1.5-2.5%. In some embodiment, the lubricant is present in an amount of about 1.5% or 1.6% or 1.7% or 1.8% or 1.9% or 2.0% or 2.1% or 2.2% or 2.3% or 2.4% or 2.5%.

The lubricant may be talc, magnesium stearate, calcium stearate, zinc stearate, glyceryl behenate, glyceryl debehenate, behenoyl polyoxyl-8 glycerides, polyethylene oxide polymers, sodium lauryl sulphate, magnesium lauryl sulphate, sodium oleate, sodium stearyl fumarate, stearic acid, hydrogenated vegetable oils, silicon dioxide and/or polyethylene glycol. In some embodiments, the lubricant is magnesium stearate.

Tablet Shape

FIGS. 1 to 8 illustrate an external form of an embodiment of a tablet of the present invention.

Figure 2:
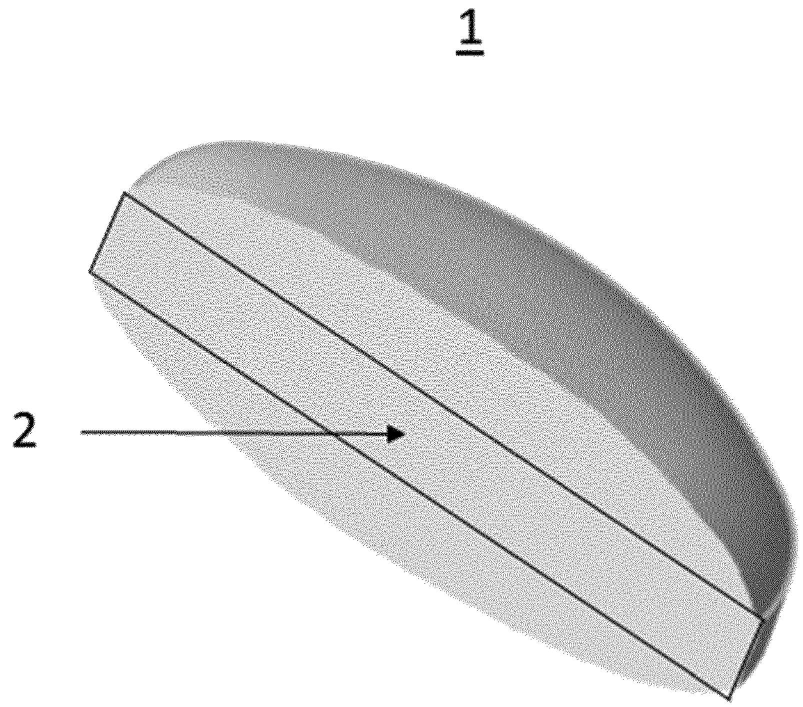
FIG. 2 is a section view along the line a-a from FIG. 1.
Figure 3:
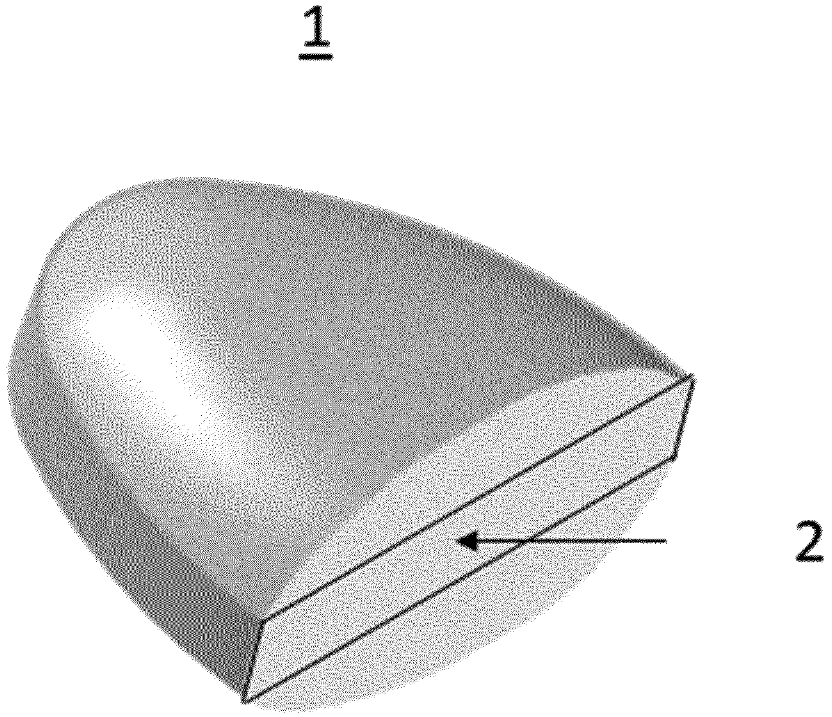
FIG. 3 is a section view along the line b-b from FIG. 1.

As shown in FIGS. 1, 2 and 3, the part/volume between the opposing cups of a tablet 1 is referred to as body 2, whereas the outside area between the opposing cups surrounding the body 2 is referred to as band 2*a*.

Figure 4:
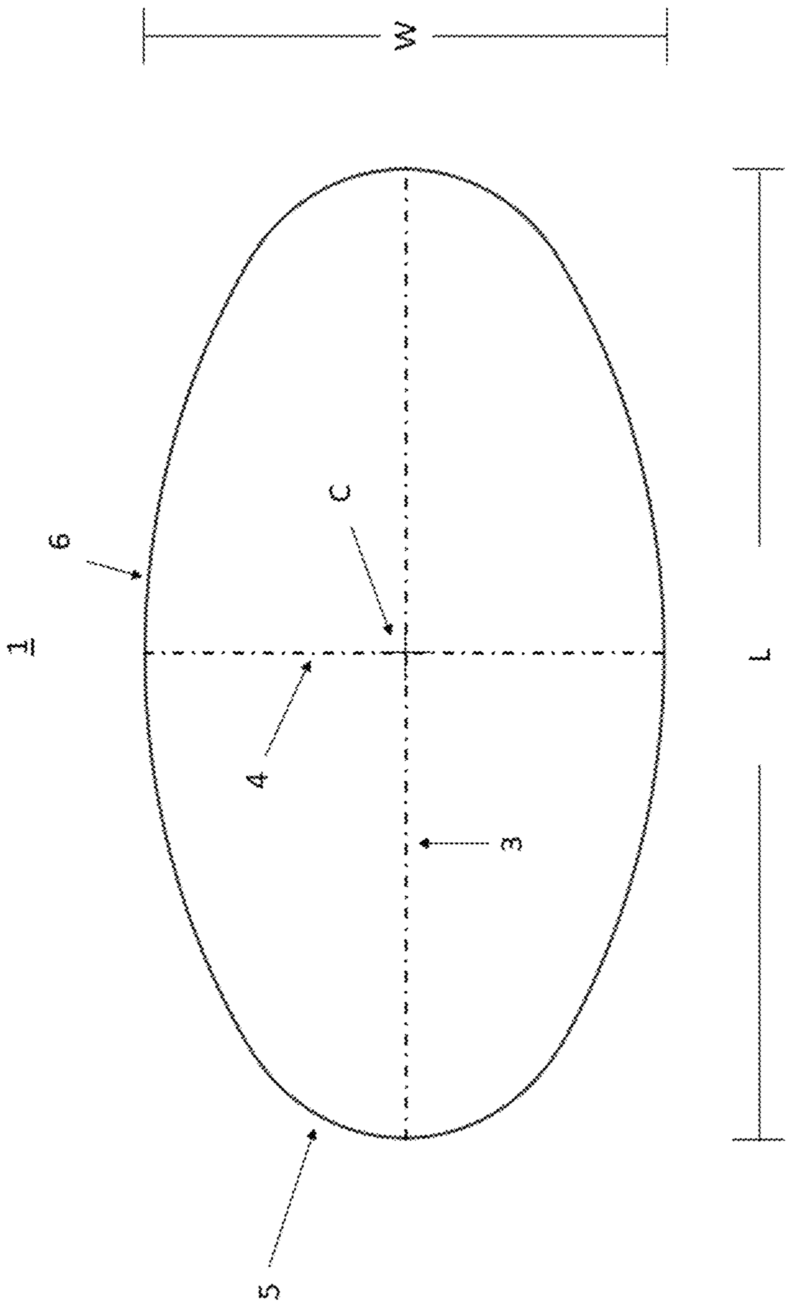
FIG. 4 is a plan top view of a tablet 1 according to the present invention.

As shown in FIG. 4, a tablet 1 is longer in one direction, when viewed from the tip face (top view). The tablet 1 may have a centre point C, also known as centroid. The tablet 1 has a major axis 3 and a minor axis 4. The major axis and the minor axis are perpendicular to each other. The major and the minor axis have a point of intersection. The point of intersection between the major and the minor axis corresponds to the centre point C. The major axis may also be referred to as longitudinal centre axis. The minor axis may also be referred to as lateral centre axis. The length L of the tablet 1 corresponds to the length of the major axis. The width W of the tablet corresponds to the length of the minor axis. The tablet 1 has an end radius 5 and a side radius 6. The end radius 5 is located at either end of the tablet 1. The side radius 6 is located at either side of the tablet 1. The side radius together with the end radius determines the shape of the body. For instance, if a shaped tablet has a body where the side radius is approaching infinity, such a tablet is referred to as capsule shaped. Put differently, the body of a tablet having a capsule configuration has only one radius, i.e. an end radius, and parallel sides. A tablet having a body defined by a side radius and an end radius is generally referred to as an oval tablet configuration and includes thus also capsule shaped tablets.

The ratio between the length of the tablet and the width of the tablet is also referred herein as "length to width ratio". If the length to width ratio is above 1.0, the tablet may also be referred to as an elongated tablet. Examples of an elongated tablet are capsule shaped or oval shaped tablets. The length to width ratio can be calculated according to formula (I).

$$\text{Length to width ratio} = \frac{\text{Length } (L)}{\text{Width } (W)} > 1.0 \quad \text{(I)}$$

Figure 5:
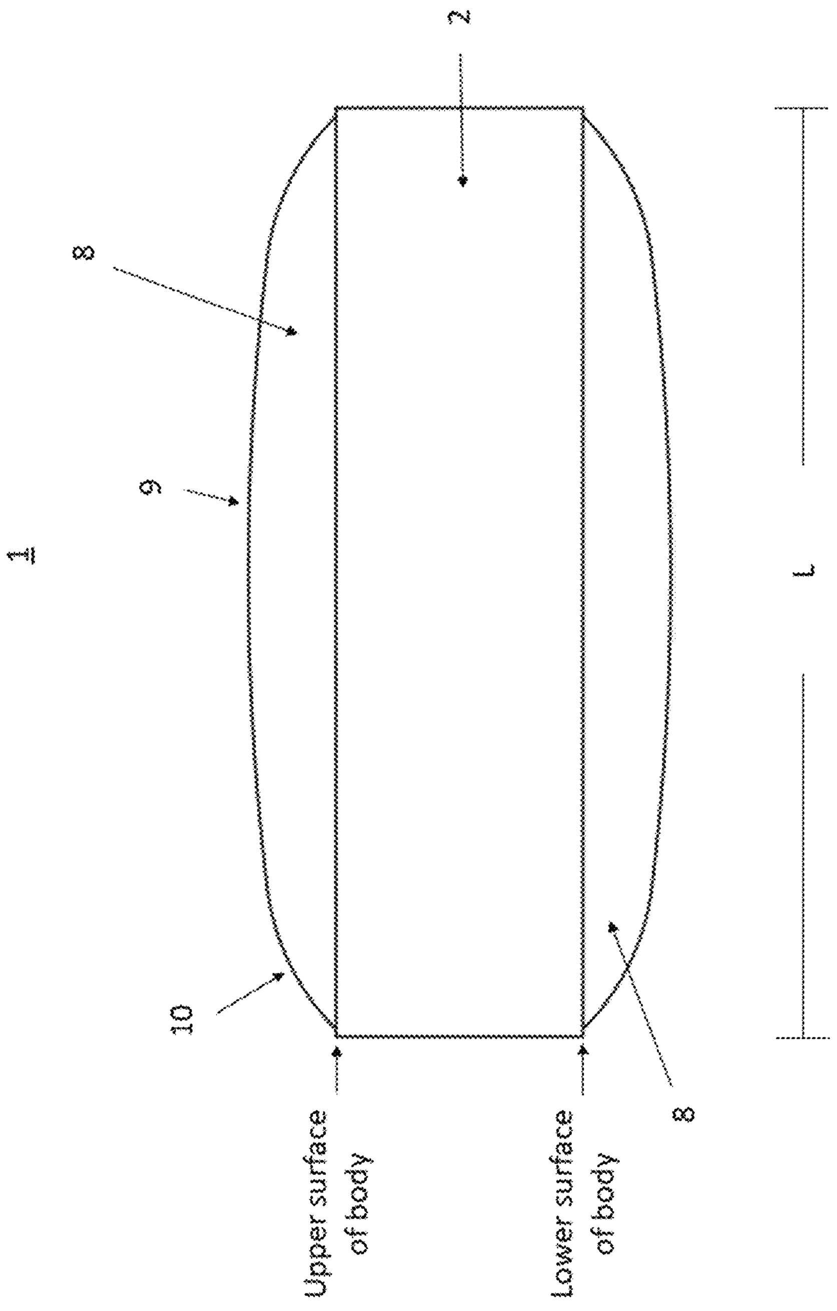
FIG. 5 is a plan side view of a tablet 1 according to the present invention.
Figure 6:
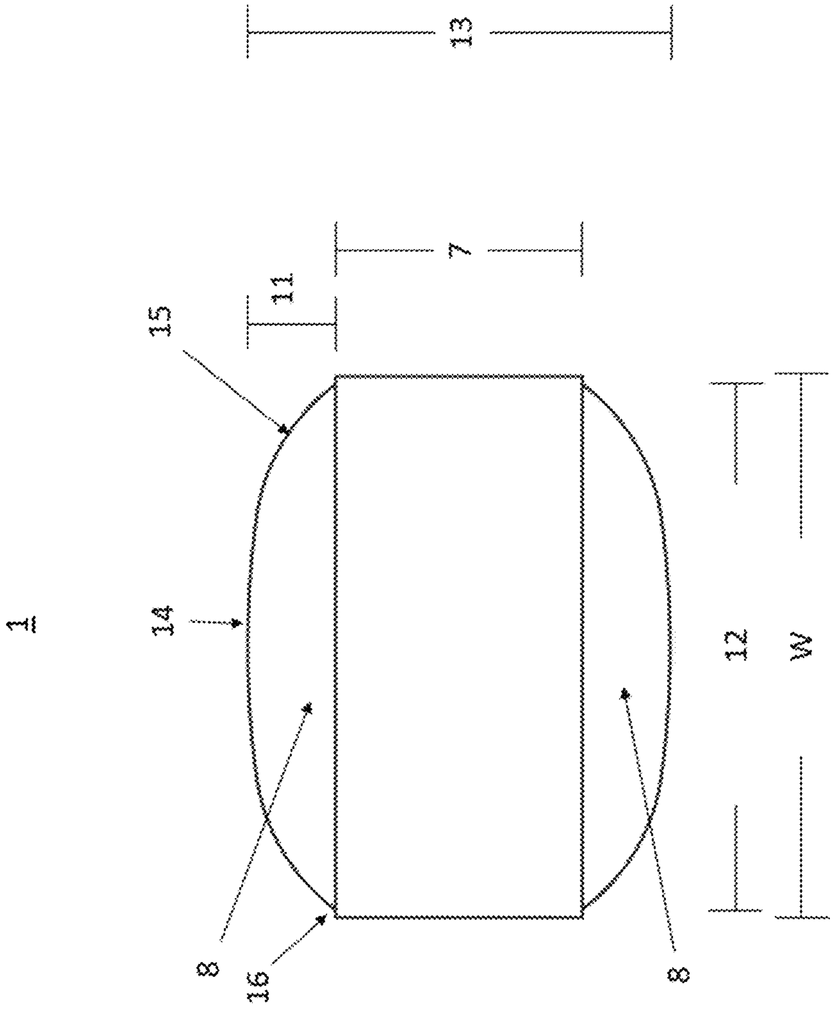
FIG. 6 is a plan front view of a tablet 1 according to the present invention.

As shown in FIGS. 5 and 6, a tablet 1 comprises a body 2. The body 2 has an upper surface and a lower surface. The body 2 has a height, also herein referred to as "core height"

7 of the tablet. The tablet 1 further comprises two opposing cups 8. The cups 8 are substantially mirror-inverted. The upper or first cup 8 is convexly formed from the upper surface of the body 2 and the lower or second cup 8 is convexly formed from the lower surface of the body 2. Each cup 8 has a major major radius 9 and a major minor radius 10.

Each cup 8 further has a minor major radius 14 and a minor minor radius 15. Tablet 1 may also comprise a land 16. If the tablet 1 does not comprise a land 16 then the cup width 12 corresponds to the width W of the tablet Each cup 8 has a cup depth 11 and a cup width 12. The total height 13 of the tablet 1 may be calculated by adding the cup depth 11 of each cup 8 and the core height 7.

The cup may be defined as shallow, standard, deep, extra-deep or modified ball according to the tableting specification manual (TMS) of the American Pharmacists Association ($7^{th}$ Edition, Section 3, page 54, TMS-N23).

Figure 7:
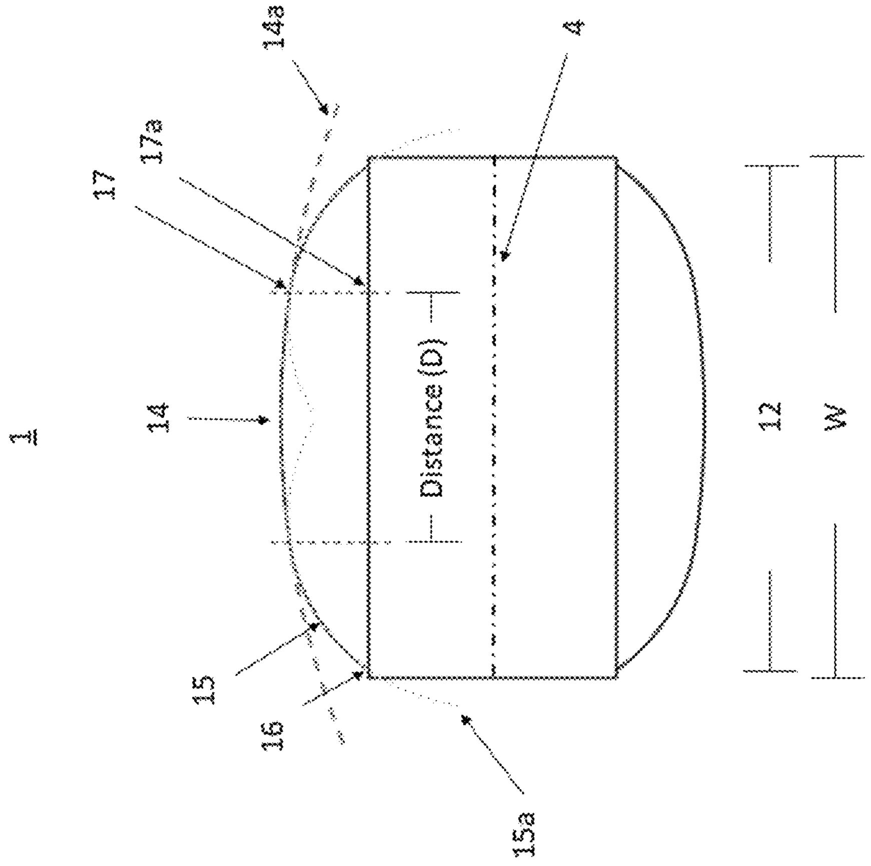
FIG. 7 is a section view along the line b-b from FIG. 1 of a tablet 1 according to the present invention showing the minor minor radius and the minor major radius as well as parts of their corresponding circles.
Figure 8:
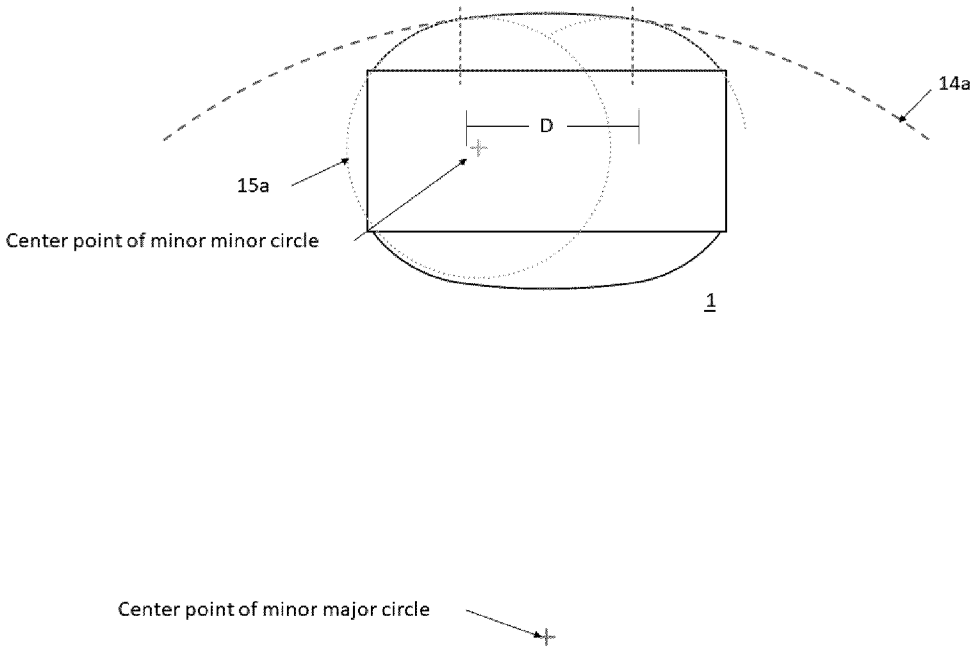
FIG. 8 is a section view along the line b-b from FIG. 1 of a tablet 1 according to the present invention further indicating the minor minor circle and the centre points of the minor minor circle and the minor major circle.

FIGS. 7 and 8 schematically show the point of intersection 17 between the minor major circle 14*a* and one of the minor minor circles (15*a*). The minor major radius 14 defines the minor major circle 14*a* and each minor minor radius 15 defines each a minor minor circle 15*a*. The points of intersection 17 have a corresponding projected point of intersection 17*a* on the surface of the body, the surface being parallel to the minor axis 4. As exemplified in FIGS. 7 and 8, the tablet 1 may have four points of intersection 17, two points of intersection per cup 8 and hence, four projected points of intersection 17*a*, two projected points of intersection per cup 8. The distance between a first projected point of intersection 17*a* and a second projected point of intersection 17 is shown in FIGS. 7 and 8 as distance (D). The distance (D) may be measured in millimetre (mm). The part of the cup width 12 constituted by the two minor minor radii 15 may be calculated according to formula (II).

$$\text{part of the cup width constituted by the minor minor radius} = \text{cup width (12)} - \text{distance } (D) \quad \text{(II)}$$

Having a compound cup instead of a standard cup allows for a greater volume. Increasing the volume of the cup will reduce the core height of the tablet, making the tablet appear thinner and easier to swallow. However, the intersection of the land with the major minor and minor minor cup radii becomes a high-stress point for the punch/punches, which is prone to failure under extreme loading, and therefore has a much lower maximum compression force than the standard cup. Extreme loading is not uncommon with the compound cup configuration. The compound cup has more volume; therefore as the upper punch cup enters the die, it entraps a larger air volume, which then must be expelled during compression. For this reason, the use of a compound cup may require slower die rotational speed and/or higher compression force and/or multiple cycles of compression forces than a standard cup and thus limiting the tableting speed and broad applicability.

The inventors have surprisingly found that when the ratio between the part of the cup width constituted by the minor minor radius (formula II) and the cup width 12 is 0.67 or below, the formation of cracks during tabletting can be drastically reduced. The ratio between the two minor minor radii parts of the cup width and the cup width 12 is defined herein as index value. Hence, tablet 1 has an index value of 0.67 or below. The index value defines the cup edge rounding and can be calculated according to formula (III) and assures that the cup is rounded narrowly enough at the sides of the cup from the land. An index value of 0.67 or below can lead to less lateral movement of powder in the cup during compression and less air may be entrapped in the centre of the cup during compression.

$$\text{Index value} = \frac{\text{cup width (12)} - \text{Distance } (D)}{\text{cup width (12)}} \leq 0.67 \quad \text{(III)}$$

The tablet height to cup depth ratio can be calculated according to formula (IV). A tablet height to cup depth ratio of above 4.3 assures that the cup is shallow or standard as defined by the tableting specification manual (TMS) of the American Pharmacists Association ($7^{th}$ Edition, Section 3, page 54, TMS-N23). An overly deep cup may exacerbate the crack formation and may prevent measures intended to reduce the crack formation. More lateral movement of powder from the periphery of the cup towards the centre of the cup may occur for deeper cups, which may cause air entrapment in the centre of the cup.

$$\text{Tablet height to cup depth ratio} = \frac{\text{Total height (13)}}{\text{Cup depth (11)}} > 4.3 \quad \text{(IV)}$$

The minor major radius to width ratio defines the cup flatness and can be calculated according to formula (V). A minor major radius to width ratio above 1.15 assures that the centre part of the cup is not overly rounded as that may exacerbate the crack formation and may prevent measures intended to reduce the crack formation. More lateral movement of powder from the periphery of the cup towards the centre of the cup may occur for rounder cups, which may lead to air entrapment in the centre of the cup.

$$\text{Minor major radius to width ratio} = \frac{\text{Minor major radius (15)}}{\text{Width } (W)} > 1.15 \quad \text{(V)}$$

The tablet height to width ratio can be calculated according to formula (VI). A tablet height to width ratio of ≤0.9 assures that the tablet height is smaller than the width.

$$\text{Tablet height to width ratio} = \frac{\text{Total height (13)}}{\text{Width } (W)} \leq 0.9 \quad \text{(VI)}$$

Without wishing to be bound by theory, it is believed that a small radius at the periphery of the cup (viewed from the front) and a much larger radius at the centre of the cup such that a large flat area is obtained where a crack would occur results in a reduction of the formation of cracks, i.e. a reduction of the number of tablets having a crack compared to the number of tablets not having a crack is obtained.

Tablet Composition

The tablet composition may comprise a salt of N-(8-(2-hydroxybenzoyl)amino)caprylic acid such as SNAC, a peptide such a GLP-1 agonist, a lubricant such as magnesium stearate and optionally at least one pharmaceutically acceptable excipient. The tablet composition may be granulated.

Salt of N-(8-(2-hydroxybenzoyl)amino)caprylic acid

The structural formula of N-(8-(2-hydroxybenzoyl) amino)caprylate is shown in chemical formula (VII).

(VII)

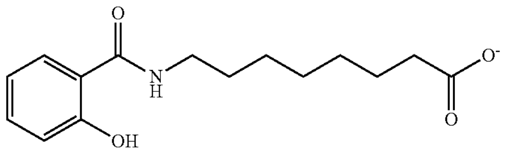

In some embodiments the salt of N-(8-(2-hydroxybenzoyl)amino)caprylic acid comprises one monovalent cation, two monovalent cations or one divalent cation. In some embodiments the salt of N-(8-(2-hydroxybenzoyl)amino) caprylic acid is selected from the group consisting of the sodium salt, potassium salt and/or calcium salt of N-(8-(2-hydroxybenzoyl)amino)caprylic acid. In one embodiment the salt of N-(8-(2-hydroxybenzoyl)amino)caprylic acid is selected from the group consisting of the sodium salt, potassium salt and/or the ammonium salt. In one embodiment the salt of N-(8-(2-hydroxybenzoyl)amino)caprylic acid is the sodium salt or the potassium salt. Salts of N-(8-(2-hydroxybenzoyl)amino)caprylate may be prepared using the method described in e.g. WO96/030036, WO00/046182, WO01/092206 or WO2008/028859. The salt of N-(8-(2-hydroxybenzoyl)amino)caprylic acid may be crystalline and/or amorphous. In some embodiments the delivery agent comprises the anhydrate, monohydrate, dihydrate, trihydrate, a solvate or one third of a hydrate of the salt of N-(8-(2-hydroxybenzoyl)amino)caprylic acid as well as combinations thereof. In some embodiments the delivery agent is a salt of N-(8-(2-hydroxybenzoyl)amino)caprylic acid as described in WO 2007/121318.

In some embodiments the delivery agent is sodium N-(8-(2-hydroxybenzoyl)amino)caprylate (referred to as "SNAC" herein), also known as sodium 8-(salicyloylamino) octanoate.

Methods of Preparation of Pharmaceutical Compositions

According to a second aspect, there is provided a process for preparing a tablet according to the first aspect. Preparation of a tablet composition according to the invention may be performed according to methods known in the art.

The process for preparing a tablet of the invention may comprise the steps of:

a. providing excipients;
b. mixing the excipients;
optionally c. granulation such as dry-granulating the excipients to obtain a granulated tablet composition,
optionally d. mixing the granules obtainable from step c with additional excipients; and
e. forming a tablet according to the first aspect of the invention in a tablet press wherein the maximal compression force to be applied to the tablet is up to 60 kN, such as 1-40 kN.

Step a.

In some embodiments, components of the tablet composition such as a salt of N-(8-(2-hydroxybenzoyl)amino) caprylic acid such as SNAC, a peptide such as a GLP-1 agonist, a lubricant such as magnesium stearate and optionally at least one pharmaceutically acceptable excipient may be provided.

Step b.

The excipients provided in step a, may be weighed, optionally delumped or sieved and then combined by mixing of the components. Mixing may be carried out until a homogeneous blend is obtained.

Step c.

The blended or mixed excipients of step b may be granulated as explained below. In some embodiments, the excipients are dry granulated. In some embodiments the excipients are wet granulated.

If granules are to be used in the tabletting material, granules may be produced in a manner known to a person skilled in the art, for example using wet granulation methods known for the production of "built-up" granules or "broken-down" granules. Methods for the formation of built-up granules may operate continuously and comprise, for example simultaneously spraying the granulation mass with granulation solution and drying, for example in a drum granulator, in pan granulators, on disc granulators, in a fluidized bed, by spray-drying, spray-granulation or spray-solidifying, or operate discontinuously, for example in a fluidized bed, in a rotary fluid bed, in a batch mixer, such as a high shear mixer or a low shear mixer, or in a spray-drying drum. Methods for the production of broken-down granules, which may be carried out discontinuously and in which the granulation mass first forms a wet aggregate with the granulation solution, which is subsequently comminuted or by other means formed into granules of the desired size and the granules may then be dried. Alternatively, the granulation liquid might be solid upon addition to the granulation mass and then melted while mixing together with the granulation mass and thus forming granules when solidified after cooling. Suitable equipment for the wet granulation step are planetary mixers, low shear mixers, high shear mixers, fluidized beds, spray-driers, extruders and spheronizers, such as an apparatus from the companies Loedige, Glatt, Diosna, Fielder, Collette, Aeschbach, Alexanderwerk, Ytron, LB Bohle, GEA, Wyss & Probst, Werner & Pfleiderer, HKD, Loser, Fuji, Nica, Caleva and Gabler. Granules may also be formed by dry granulation techniques in which one or more of the excipient(s) and/or the active pharmaceutical ingredient is compressed to form relatively large moldings, for example slugs or ribbons, which are comminuted by grinding, and the ground material serves as the tabletting material to be later compacted. Suitable equipment for dry granulation is, but not limited to, roller compaction equipment from Alexanderwerk, Freund-Vector, Gerteis, and LB Bohle.

Step d.

The granules provided in step c and alternatively other excipients, may be weighed, optionally delumped or sieved and then combined by mixing. Mixing may be carried out until a homogeneous blend is obtained.

Step e.

An excess quantity of the tableting material such as the granulated excipients obtainable in step c. and/or d. may be supplied to the die cavity with a lower punch and an upper punch. Consecutively, an exact quantity of the tableting material may be metered out to match the desired tablet weight by pushing out excess tableting material. Subsequently, the excess quantity may be removed by a scraping action. The supply of the tableting material can be facilitated by gravity or mechanically forced by use of e.g. rotating baffles placed just above the die cavity.

The metered out tableting material may be compacted inside the die cavity by a set of punches such as an upper punch and a lower punch exerting a pressure obtained by reducing the distance between the tips of the upper and lower punches. Pressure can be applied once or multiple times. Pressure may be applied twice. Applying pressure in a first round, also referred to as "pre-compression" can remove air and can orient particles of the tableting material in a denser packing. Subsequently, pressure is applied again in a second round, also referred to as "main compression" allowing the particles to fragment and deform elastically and/or plastically to result in the desired tablet properties. The pressure of the pre-compression can be lower than the pressure of the main compression. The pressure of the pre-compression can also be high enough to result in particle fragmentation and elastic and/or plastic deformation. The main pressure and the pre-compression may be derived by measuring the force required for bringing the punch tips closer to each other and then transforming that into a pressure by compensating for the cup area and optionally for the shape of body. Subsequently, the tablet can be ejected from the die cavity by first removing the upper punch and then by pushing the tablet out of the die cavity by use of the lower punch. A guide or scraper may be used to direct the ejected tablet automatically away from the die table and onto a chute leading the tablet out from the tableting machine. The thickness of the so-obtained tablet is related to the minimum distance between the tips of the upper and lower punches during the main compression. The breaking force of the so-obtained tablets is related to the number of times pressure is exerted, the maximally reached pressure and the dwell time for exerting the pressure. Suitable tablet presses include, but are not limited to, rotary tablet presses and eccentric tablet presses such as an apparatus from Fette, Korsch, Manesty, GEA, Courtoy, and Riva Piccola.

In a third aspect, there is provided a punch set comprising an upper punch, a lower punch, and a die or die cavity, also called a punch set, a tooling set, or a station, for making a tablet according to the first aspect. The punches can have a single tip or multiple tips. The die or die cavity can be tapered or non-tapered.

In some embodiments, the punch set enables (a) a tablet height to width ratio of 0.9 or below, such as of about 0.05-0.9; (b) a tablet height to cup depth ratio of above 4.3, such as of about 4.4-100; (c) a minor major radius to width ratio of above 1.15, such as of about 1.16-100; and/or (d) an index value of 0.67 or below, such as of about 0.05-0.55.

Pharmaceutical Indications

In a fourth aspect, there is provided a tablet according to the first aspect of the invention for use in medicine. The composition of the invention may be used for the following medical treatments, all preferably relating one way or the other to diabetes and/or obesity:

(i) prevention and/or treatment of all forms of diabetes, such as hyperglycemia, type 2 diabetes, impaired glucose tolerance, type 1 diabetes, non-insulin dependent diabetes, MODY (maturity onset diabetes of the young), gestational diabetes, and/or for reduction of HbA1C;

(ii) delaying or preventing diabetic disease progression, such as progression in type 2 diabetes, delaying the progression of impaired glucose tolerance (IGT) to insulin requiring type 2 diabetes, and/or delaying the progression of non-insulin requiring type 2 diabetes to insulin requiring type 2 diabetes;

(iii) improving β-cell function, such as decreasing β-cell apoptosis, increasing β-cell function and/or β-cell mass, and/or for restoring glucose sensitivity to β-cells;

(iv) prevention and/or treatment of cognitive disorders;

(v) prevention and/or treatment of eating disorders, such as obesity, e.g. by decreasing food intake, reducing body weight, suppressing appetite, inducing satiety; treating or preventing binge eating disorder, bulimia nervosa, and/or obesity induced by administration of an antipsychotic or a steroid; reduction of gastric motility; and/or delaying gastric emptying;

(vi) prevention and/or treatment of diabetic complications, such as neuropathy, including peripheral neuropathy; nephropathy; or retinopathy;

(vii) improving lipid parameters, such as prevention and/or treatment of dyslipidemia, lowering total serum lipids; lowering HDL; lowering small, dense LDL; lowering VLDL: lowering triglycerides; lowering cholesterol; increasing HDL; lowering plasma levels of lipoprotein a (Lp(a)) in a human; inhibiting generation of apolipoprotein a (apo(a)) in vitro and/or in vivo;

(iix) prevention and/or treatment of cardiovascular diseases, such as syndrome X; atherosclerosis; myocardial infarction; coronary heart disease; stroke, cerebral ischemia; an early cardiac or early cardiovascular disease, such as left ventricular hypertrophy; coronary artery disease; essential hypertension; acute hypertensive emergency; cardiomyopathy; heart insufficiency; exercise tolerance; chronic heart failure; arrhythmia; cardiac dysrhythmia; syncopy; atheroschlerosis; mild chronic heart failure; angina pectoris; cardiac bypass reocclusion; intermittent claudication (atheroschlerosis oblitterens); diastolic dysfunction; and/or systolic dysfunction;

(ix) prevention and/or treatment of gastrointestinal diseases, such as inflammatory bowel syndrome; small bowel syndrome, or Crohn's disease; dyspepsia; and/or gastric ulcers;

(x) prevention and/or treatment of critical illness, such as treatment of a critically ill patient, a critical illness poly-nephropathy (CIPNP) patient, and/or a potential CIPNP patient; prevention of critical illness or development of CIPNP; prevention, treatment and/or cure of systemic inflammatory response syndrome (SIRS) in a patient; and/or for the prevention or reduction of the likelihood of a patient suffering from bacteraemia, septicaemia, and/or septic shock during hospitalisation; and/or (xi) prevention and/or treatment of polycystic ovary syndrome (PCOS).

In some embodiment, the indication is selected from the group consisting of (i)-(iii) and (v)-(iix), such as indications (i), (ii), and/or (iii); or indication (v), indication (vi), indication (vii), and/or indication (iix). In another particular embodiment, the indication is (i). In a further particular embodiment the indication is (v). In a still further particular embodiment the indication is (iix). In some embodiments the indications are type 2 diabetes and/or obesity.

In a fifth aspect, there is provided a tablet according to the first aspect of the invention for use in the treatment of diabetes or obesity.

Method of Treatment

In an alternative fourth aspect, there is provided method of treating a subject in need thereof, comprising administering a tablet according to the first aspect to a patient in need thereof. In one embodiment, the tablet is administered orally. In one embodiment the method of treatment is for treatment of diabetes or obesity and/or the further indications specified above. In some embodiments, the tablet is administered once daily or less frequent such as once weekly.

Definitions

As used herein, the term "about" or "approximately", when used together with a numeric value (e.g. 5, 10%, ⅓), refers to a range of numeric values that can be less or more than the number. In some embodiments, the term "about" as used herein means±10% of the value referred to, and includes the value. For example, "about 5" refers to a range of numeric values that are 10%, 5%, 2%, or 1% less or more than 5, e.g. a range of 4.5 to 5.5, or 4.75 to 5.25, or 4.9 to 5.1, or 4.95 to 5.05.

Unless the context dictates the contrary, all ranges set forth herein should be interpreted as being inclusive of their endpoints and open-ended ranges should be interpreted to include only commercially practical values. Similarly, all lists of values should be considered as inclusive of intermediate values unless the context indicates the contrary.

The term "excipient" as used herein broadly refers to any component other than the active therapeutic ingredient(s) or active pharmaceutical ingredient(s) (API(s)).

The excipient may be a pharmaceutically inert substance, an inactive substance, and/or a therapeutically or medicinally non-active substance. The excipient may serve various purposes, e.g. as a carrier, vehicle, filler, binder, lubricant, glidant, disintegrant, flow control agent, crystallization inhibitors solubilizer, stabilizer, colouring agent, flavouring agent, surfactant, emulsifier or combinations of thereof and/or to improve administration, and/or absorption of the therapeutically active substance(s) or active pharmaceutical ingredient(s). The amount of each excipient used may vary within ranges conventional in the art. Techniques and excipients which may be used to formulate oral dosage forms are described in Handbook of Pharmaceutical Excipients, 8th edition, Sheskey et al., Eds., American Pharmaceuticals Association and the Pharmaceutical Press, publications department of the Royal Pharmaceutical Society of Great Britain (2017); and Remington: the Science and Practice of Pharmacy, 22nd edition, Remington and Allen, Eds., Pharmaceutical Press (2013).

The term "tablet composition" as used herein is an umbrella term to encompass the excipients of the tablet according to the invention.

By "tableting" we mean the function of compressing a volume of powder or granular material into a single unit of hard form.

"Tableting material" is an umbrella term for the various components/excipients making up the tablet and/or tablet composition as described herein.

The term "body" of the tablet as used herein refers to the volume between the opposing cups.

The term "band" of the tablet as used herein refers to the outside area of the surface of the body between the opposing cups.

By "compound cup" we mean a cup design in which multiple arcs or radii are generated from the cup's centre point across the cup's diameter, minor axis or major axis.

The term "radius" such as e.g. "major major radius", "major minor radius", "minor major radius", "minor minor radius" refers to a single arc generated from a centre point. The term "circle" refers to the circle generated by the radius. A graphical example is provided in FIG. 8 for the minor minor radius and minor minor circle, respectively. The various radii can be calculated using the software Tablet-CAD (Natoli Engineering Company, Inc.).

A "standard cup" design is a cup design in which a single arc or radius is generated from the cup's centre point across the cup's diameter, minor, or major axis.

"Cup depth" is the distance from the cup's lowest point (usually the cup's centre point) to its highest point (usually the highest point of the land). By "land" we mean a narrow plane perpendicular to the tablet's band, which creates a junction between the band and the cup.

"Capping" is when the upper or lower cup of the tablet separates horizontally either partially or completely, from the body of the tablet.

"Chipping" is a defect in the tablet in which a piece has broken off around the edge.

"Organoleptic properties" are the aspects of food, water or other substances that create an individual experience via the senses—including taste, sight, smell, sound, and touch. As used herein, the term mainly addresses the "swallowability" of a tablet e.g. the willingness of a patient to swallow a tablet based on the appearance of a tablet in terms of size as well as in terms of the presence of cracks and flaws on the tablet's surface.

As used herein, the "median particle size (D50)" refers to the particle size value where 50% of the particle sizes are smaller and 50% of the particle sizes are larger.

The terms "granulate" and "granules" are used interchangeably herein to refer to particles of composition material which may be prepared as described above.

The term "maximum compression force" includes pre-compression force(s) and main compression force as well as a combination there of.

The term "tablet density" as used herein refers to the tablet mass divided by the tablet envelope volume where the tablet envelope volume can be derived from the measured tablet height, the cup volume, the cup depth, and the cross-sectional area of the body 2 (the area as shown in the plan top view of FIG. 4). Such a derived tablet volume is called the "tablet envelope volume" as it includes all internal voids inside the tablets such as pores and closed cavities and the volume comprises thus the tablet in its entirety.

The term "tablet porosity" as used herein refers to the fraction of void space inside the tablet (such as internal pores and cavities) calculated as a percentage between 0-100% of the tablet volume (such as the tablet envelope volume as described above). To calculate the tablet porosity, the tablet density is calculated as described above, and assuming a maximum tablet density (i.e. at 0% porosity and thus at a solid fraction equalling 1) of 1.28 g/mL, the solid fraction can be calculated as the tablet density divided by the maximum tablet density of 1.28 g/mL. The porosity is then 1 minus the solid fraction and converted into a percentage between 0-100%.

The term "GLP-1 agonist" as used herein refers to a compound, which fully or partially activates the human GLP-1 receptor. The term is thus equal to the term "GLP-1 receptor agonist" used in other documents. The term GLP-1 agonist as well as the specific GLP-1 agonists described herein are meant to encompass also salt forms hereof.

It follows that the GLP-1 agonist should display "GLP-1 activity" which refers to the ability of the compound, i.e. a GLP-1 analogue or a compound comprising a GLP-1 analogue, to bind to the GLP-1 receptor and initiate a signal transduction pathway resulting in insulinotropic action or other physiological effects as is known in the art.

All headings and sub-headings are used herein for convenience only and should not be constructed as limiting the invention in any way.

The use of any and all examples, or exemplary language (e.g. such as) provided herein, is intended merely to better illuminate the invention and does not pose a limitation on the scope of the invention unless otherwise claimed. No language in the specification should be construed as indicating any non-claimed element as essential to the practice of the invention.

The citation and incorporation of patent documents herein is done for convenience only and does not reflect any view of the validity, patentability, and/or enforceability of such patent documents.

This invention includes all modifications and equivalents of the subject matter recited in the claims appended hereto as permitted by applicable law.

EMBODIMENTS

1. A tablet 1 comprising a salt of N-(8-(2-hydroxybenzoyl)amino)caprylic acid in a total amount of about 60 to 99.8% in weight based on the total weight of the tablet, the tablet having
   (a) a tablet height to width ratio of 0.9 or below, such as of about 0.05-0.9;
   (b) a tablet height to cup depth ratio of above 4.3, such as of about 4.4-100;
   (c) a minor major radius to width ratio of above 1.15, such as of about 1.16-100; and/or
   (d) an index value of 0.67 or below, such as of about 0.05-0.67.
2. The tablet according to embodiment 1, wherein the tablet is elongated.
3. The tablet according to embodiment 1 or embodiment 2, wherein the tablet is a compound cup tablet.
4. A tablet 1 comprising a salt of N-(8-(2-hydroxybenzoyl)amino)caprylic acid in a total amount of about 60 to 99.8% in weight based on the total weight of the tablet, wherein the tablet further comprises
   a body 2 having an upper and a lower surface, a side radius 6, an end radius 5, a major axis 3 and a minor axis 4; and
   two substantially mirror-inverted or opposing cups 8, wherein the first cup 8 is convexly formed from the upper surface of the body and the second cup 8 is convexly formed from the lower surface of the body, and wherein
   each cup has a cup depth 11, a cup width 12, a major major radius 9, two substantially identical major minor radii 10, a minor major radius 14 and two substantially identical minor minor radii 15, wherein the tablet has
   (a) a tablet height to width ratio of 0.9 or below; such as of about 0.05-0.9;
   (b) a tablet height to cup depth ratio of above 4.3 such as of about 4.4-100;
   (c) a minor major radius to width ratio of above 1.15, such as of about 1.16-100;
   (d) an index value of 0.67 or below, such as of about 0.05-0.67; and/or
   (e) a major axis to minor axis ratio of above 1.0, such as of about 1.1-100.
5. The tablet according to any one of embodiments 1-4, wherein the tablet is oval-shaped or capsule shaped.
6. The tablet according to any one of embodiments 1-5, wherein the tablet height to width ratio is about 0.1-0.9, such as about 0.2-0.9, such as about 0.3-0.9, such as about 0.4-0.9.
7. The tablet according to any one of embodiments 1-6, wherein the tablet height to cup depth ratio is about 4.4-50, such as 4.4-30, such as about 4.4-20, such as about 4.4-20, such as about 4.4-15, such as about 4.4-10.
8. The tablet according to any one of embodiments 1-7, wherein the minor major radius to width ratio is about 1.16-50, such as about 1.16-30, such as about 1.16-15.

9. The tablet according to any one of embodiments 1-8, wherein the index value is about 0.10-0.67, such as about 0.15-0.67.
10. The tablet according to any one of embodiments 1-9, wherein the total weight of the tablet is about 50 to 1200 mg.
11. The tablet according to any one of embodiments 1-10, wherein the total weight of the tablet is about 90 to 190 mg, such as about 100-175 mg.
12. The tablet according to embodiment 11, wherein the major axis is about 7.1-10.0, such as about 8.6 mm.
13. The tablet according to embodiment 11 or embodiment 12, wherein the minor axis is about 3.6-6.1 mm, such as about 4.9 mm.
14. The tablet according to any one of embodiments 11-13, wherein the side radius is about 5.7-9.4, such as about 6.7 mm.
15. The tablet according to any one of embodiments 11-14, wherein the end radius is about 1.3-2.1 mm, such as about 1.7 mm.
16. The tablet according to any one of embodiments 11-15, wherein the cup depth is about 0.5-1.1 mm, such as about 0.8 mm.
17. The tablet according to any one of embodiments 11-16, wherein the major major radius is above 13.8 mm, such as about 25.0 mm.
18. The tablet according to any one of embodiments 11-17, wherein the major minor radius is below 11.4 mm, such as about 2.3 mm.
19. The tablet according to any one of embodiments 11-18, wherein the minor major radius is above 4.7 mm, such as about 8.6 mm.
20. The tablet according to any one of embodiments 11-19, wherein the minor minor radius is below 3.6 mm, such as about 1.8 mm.
21. The tablet according to any of embodiments 11-20, wherein
   (a) the height to width ratio is about 0.7;
   (b) the tablet height to cup depth ratio is about 4.5;
   (c) the minor minor radius to width ratio is of about 1.40 and/or
   (d) the index value is about 0.67.
22. The tablet according to any one of embodiments 1-10, wherein the total weight of the tablet is about 190 to 290 mg, such as about 200-280 mg.
23. The tablet according to embodiment 22, wherein the major axis is about 8.7-12.2 mm, such as about 10.4 mm.
24. The tablet according to embodiment 22 or embodiment 23, wherein the minor axis is about 4.4-7.4 mm, such as about 5.9 mm.
25. The tablet according to any one of embodiments 22-24, wherein the side radius is about 6.9-11.4 mm, such as about 8.2 mm.
26. The tablet according to any one of embodiments 22-25, wherein the end radius is about 1.6-2.6 mm, such as about 2.1 mm.
27. The tablet according to any one of embodiments 22-26, wherein the cup depth is about 0.6-1.3 mm, such as about 1.0 mm.
28. The tablet according to any one of embodiments 22-27, wherein the major major radius is above 16.7 mm, such as about 30.4 mm.
29. The tablet according to any one of embodiments 22-28, wherein the major minor radius is below 13.9 mm, such as about 2.8 mm.

30. The tablet according to any one of embodiments 22-39, wherein the minor major radius is above 5.7 mm, such as about 10.4 mm.
31. The tablet according to any one of embodiments 22-40, wherein the minor minor radius is below 4.3 mm, such as about 2.2 mm.
32. The tablet according to any one of embodiments 1-10, wherein the total weight of the tablet is about 290 to 390 mg, such as about 300-380 mg.
33. The tablet according to embodiment 32, wherein the major axis is about 10.0-14.0 mm, such as about 12 mm.
34. The tablet according to embodiment 32 or embodiment 33, wherein the minor axis is about 5.1-8.5 mm such as about 6.8 mm.
35. The tablet according to any one of embodiments 32-34, wherein the side radius is about 8.0-13.1 mm such as about 9.4 mm.
36. The tablet according to any one of embodiments 32-35, wherein the end radius is about 1.8-3.0 mm such as 2.4 mm.
37. The tablet according to any one of embodiments 32-36, wherein the cup depth is about 0.7 to 1.5 mm, such as about 1.1 mm.
38. The tablet according to any one of embodiments 32-37, wherein the major major radius is above 19.3 mm, such as about 35 mm.
39. The tablet according to any one of embodiments 32-38, wherein the major minor radius is below 16.0 mm, such as about 3.2 mm.
40. The tablet according to any one of embodiments 32-39, wherein the minor major radius is above 6.6 mm, such as about 12.00.
41. The tablet according to any one of embodiments 32-40, wherein the minor minor radius is below 5.0 mm, such as about 2.5 mm.
42. The tablet according to any one of embodiments 32-41, wherein
(a) the height to width ratio is about 0.8;
(b) the tablet height to cup depth ratio is about 4.8;
(c) the minor major radius to width ratio of about 1.76 and/or
(d) the index value is about 0.50.
43. The tablet according to any one of embodiments 1-10, wherein the total weight of the tablet is about 390 to 490 mg, such as about 400-485 mg.
44. The tablet according to embodiment 43, wherein the major axis is about 11.1-15.6 mm, such as 13.3 mm.
45. The tablet according to embodiment 43 or embodiment 44, wherein the minor axis is about 5.7-9.4 mm such as about 7.6 mm.
46. The tablet according to any one of embodiments 43-45, wherein the side radius is about 8.9-14.6 mm such as about 10.4 mm.
47. The tablet according to any one of embodiments 43-46, wherein the end radius is about 2.0-3.3 mm such as 2.7 mm.
48. The tablet according to any one of embodiments 43-47, wherein the cup depth is about 0.7-1.7 mm, such as about 1.2 mm.
49. The tablet according to any one of embodiments 43-48, wherein the major major radius is above 21.4 mm, such as about 38.9 mm.
50. The tablet according to any one of embodiments 43-50, wherein the major minor radius is below 17.8 mm, such as about 3.6 mm.
51. The tablet according to any one of embodiments 43-51, wherein the minor major radius is above 7.3 mm, such as about 13.3 mm.
52. The tablet according to any one of embodiments 43-52, wherein the minor minor radius is below 5.6 mm, such as about 2.8 mm.
53. The tablet according to any one of embodiments 1-10, wherein the total weight of the tablet is about 490 to 590 mg, such as about 500-585 mg.
54. The tablet according to embodiment 53, wherein the major axis is about 11.7-16.5 mm, such as 14.3 mm.
55. The tablet according to embodiment 53 or embodiment 54, wherein the minor axis is about 6.0-10.0 mm, such as 8.1 mm.
56. The tablet according to any one of embodiments 53-55, wherein the side radius is about 9.4-15.4 mm such as 11.0 mm.
57. The tablet according to any one of embodiments 53-56, wherein the end radius is about 2.1-3.5 mm, such as 2.8 mm.
58. The tablet according to any one of embodiments 53-57, wherein the cup depth is about 0.8-1.8 mm, such as 1.2 mm.
59. The tablet according to any one of embodiments 53-58, wherein the major major radius is above 22.6 mm, such as 40.0 mm.
60. The tablet according to any one of embodiments 53-59, wherein the major minor radius is below 18.8 mm, such as 3.0 mm.
61. The tablet according to any one of embodiments 53-60, wherein the minor major radius is above 7.8 mm, such as 12.0 mm.
62. The tablet according to any one of embodiments 53-61, wherein the minor minor radius is below 5.9, such as 2.5 mm.
63. The tablet according to any one of embodiments 1-10, wherein the total weight of the tablet is about 590 to 850 mg, such as about 600-830 mg.
64. The tablet according to embodiment 63, wherein the major axis is about 12.9-18.2 mm, such as 15.6 mm.
65. The tablet according to embodiment 63 or embodiment 64, wherein the minor axis is about 6.6-11.0 mm, such as 8.8 mm.
66. The tablet according to any one of embodiments 63-65, wherein the side radius is about 10.4-17.1 mm such as 12.2 mm.
67. The tablet according to any one of embodiments 63-66, wherein the end radius is about 2.3-3.9 mm, such as 3.1 mm.
68. The tablet according to any one of embodiments 63-67, wherein the cup depth is about 0.9-2.0 mm, such as 1.4 mm.
69. The tablet according to any one of embodiments 63-68, wherein the major major radius is above 25.0 mm, such as 45.5 mm.
70. The tablet according to any one of embodiments 63-69, wherein the major minor radius is below 20.8 mm, such as 4.2 mm.
71. The tablet according to any one of embodiments 63-70, wherein the minor major radius is above 8.6 mm, such as 15.6 mm.
72. The tablet according to any one of embodiments 63-71, wherein the minor minor radius is below 6.5, such as 3.2 mm.
73. The tablet according to any one of embodiments 1-10, wherein the total weight of the tablet is about 850-1200 mg, such as about 860-1150 mg.

74. The tablet according to embodiment 73, wherein the major axis is about 14.2-20.1 mm., such as 17.1 mm.
75. The tablet according to embodiment 73 or embodiment 74, wherein the minor axis is about 7.3-12.1 mm., such as 9.7 mm.
76. The tablet according to any one of embodiments 73-75, wherein the side radius is about 11.4-18.8 mm., such as 13.4 mm.
77. The tablet according to any one of embodiments 73-76, wherein the end radius is about 2.6-4.3 mm, such as 3.4 mm.
78. The tablet according to any one of embodiments 73-77, wherein the cup depth is about 0.9-2.2 mm, such as 1.6 mm.
79. The tablet according to any one of embodiments 73-78, wherein the major major radius is above 27.5 mm, such as 50.0 mm.
80. The tablet according to any one of embodiments 73-79, wherein the major minor radius is below 22.9., such as 4.6 mm.
81. The tablet according to any one of embodiments 73-80, wherein the minor major radius is above 9.4 mm such as 17.1 mm.
82. The tablet according to any one of embodiments 73-81, wherein the minor minor radius is below 7.1 mm, such as 3.6 mm.
83. The tablet according to any one of the preceding embodiments, wherein the tablet has a land of about 0.0-0.3 such as about 0.05-0.2 mm.
84. The tablet according to any one of the preceding embodiments, wherein the tablet has a land of about 0.08-0.15 mm such as about 0.1 mm.
85. The tablet according to any one of the preceding embodiments, wherein the salt of N-(8-(2-hydroxybenzoyl)amino)caprylic acid is present in a total amount of about 75-99%, such as about 79-90% in weight based on the total weight of the tablet.
86. The tablet according to any one of the preceding embodiments, wherein the salt of N-(8-(2-hydroxybenzoyl)amino)caprylic acid is present in a total amount of about 80-99%, such as 85-99% or 90-99% in weight based on the total weight of the tablet.
87. The tablet according to any one of the preceding embodiments, wherein the salt of N-(8-(2-hydroxybenzoyl)amino)caprylic acid is present in a total amount of about 85-99%, such as 90-99% or 90-98% in weight based on the total weight of the tablet.
88. The tablet according to any one of the preceding embodiments, wherein the salt of N-(8-(2-hydroxybenzoyl)amino)caprylic acid is granulated.
89. The tablet according to any one of the preceding embodiments, wherein the salt of N-(8-(2-hydroxybenzoyl)amino)caprylic acid is sodium N-(8-(2-hydroxybenzoyl)amino)caprylate (SNAC).
90. The tablet according to any one of the preceding embodiments, wherein the tablet further comprises an active pharmaceutical ingredient (API).
91. The tablet according to embodiment 90, wherein the API is present in a total amount of about 0.1-40% in weight based on the total weight of the tablet.
92. The tablet according to embodiments 90 or 91, wherein the API is a peptide.
93. The tablet according to any one of embodiments 90-92, wherein the API is present in about 0.1-14%, such as in about 0.2-10% or 0.5-8%, based on the total weight of the tablet.
94. The tablet according to any one of embodiment 90-92, wherein the API is present in about 0.1 to 30%, based on the total weight of the tablet.
95. The tablet according to any one of embodiment 90-92, wherein the API is present in about 10-35%, based on the total weight of the tablet.
96. The tablet according to any one of embodiment 90-95, wherein the peptide is a GLP-1 agonist.
97. The tablet according to any one of embodiments 90-96, wherein the API is semaglutide.
98. The tablet according to any one of the preceding embodiments, wherein the tablet further comprises a lubricant.
99. The tablet according to embodiment 98, wherein the lubricant is present in a total amount of about 0.1-7% such as about 0.5-5%, such as about 1-3%, such as about 1.5-2.5% based on the total weight of the tablet.
100. The tablet according to embodiment 98 or embodiment 99, wherein the lubricant is selected from the list consisting of talc, magnesium stearate, calcium stearate, zinc stearate, glyceryl behenate, glyceryl debehenate, behenoyl polyoxyl-8 glycerides, polyethylene oxide polymers, sodium lauryl sulfate, magnesium lauryl sulfate, sodium oleate, sodium stearyl fumarate, stearic acid, hydrogenated vegetable oils, silicon dioxide and polyethylene glycol.
101. The tablet according to any one of embodiments 98-100, wherein the lubricant is magnesium stearate.
102. The tablet according to any one of the preceding embodiments, wherein the tablet further comprises one or more pharmaceutically acceptable excipient.
103. The tablet according to any one of the preceding embodiments, wherein the tablet essentially consists of 84-97% SNAC, 0.1-14% semaglutide and 1.5-3.5% magnesium stearate, based on the total weight of the tablet.
104. The tablet according to any one of embodiments 1-102, wherein the tablet essentially consists of 65-93% SNAC, 0.1-33% semaglutide and 1.5-3.5% magnesium stearate, based on the total weight of the tablet.
105. The tablet according to any one of embodiments 1-102, wherein the tablet essentially consists of 88-97% SNAC, 0.1-9% semaglutide and 1.5-3.5% magnesium stearate, based on the total weight of the tablet.
106. The tablet according to any one of the embodiments 1-105, wherein the cup is a compound cup having two or more radii such as three or four radii per axis.
107. The tablet according to embodiment 1-106, wherein the salt of N-(8-(2-hydroxybenzoyl)amino)caprylic acid, the API, the lubricant and/or the one or more pharmaceutical excipients are granulated and the granules have median particle size (D50) of between 0.1-2000 μm.
108. The tablet according to embodiment 107, wherein the granules have a median particle size of between 100-1000 μm, such as 150-800 μm, such as 200-600 μm.
109. The tablet according to embodiments 107 or 108, wherein the median particle size is measured by a laser diffraction method.
110. The tablet according to any one of embodiments 1-109, wherein the tablet is an embossed or debossed tablet.
111. The tablet according to any one of embodiments 1-110, wherein the tablet is a coated tablet.

112. A tablet according to any one of the preceding embodiments for use in medicine.
113. A tablet according to any one of the preceding embodiments for use in the treatment of diabetes or obesity.
114. A method for treatment of diabetes or obesity comprising administering the tablet according to any one of embodiments 1-111 to a patient in need thereof.
115. The method according to embodiment 114, wherein the tablet is administered orally.
116. The method according to embodiment 114 or embodiment 115, wherein the tablet is administered once daily or less frequent such as once weekly.
117. Use of a tablet according to any one of the embodiments 1-111 for the manufacture of a medicament.
118. A process for preparing a tablet, comprising the steps of:
   a. providing excipients;
   b. mixing the excipients;
   optionally c. granulating such as dry-granulating the excipients to obtain a granulated tablet composition;
   optionally d. sieving the granulated excipients;
   optionally e. mixing the granulates obtainable from step c with additional excipients and
   f. forming a tablet according to any one of embodiments 1-111 in a tablet press wherein the maximal compression force to be applied to the tablet is up to 60 kN, such as 1-40 kN, and optionally wherein the so-formed tablet has a tablet porosity of between about 0-30% such as between about 5-25% such as between about 8-18%.
119. The process according to embodiment 118, wherein the compression force is the maximum compression force applied during a pre-compression and/or main compression.
120. A process of preparing a tablet according to any one of embodiments 1-111, wherein said process comprises the steps of:
   a) placing tableting material in a die cavity;
   b) placing a lower punch into a die from the bottom and an upper punch from above, and optionally at least one of said lower and upper punches having a tip configured to emboss or deboss said tablet with at least one character;
   c) applying pressure to the punches
   d) ejecting the tablet from the die; and
   optionally e) coating the tablet.
121. The process according to embodiment 120, where the at least one character is selected from the groups consisting of a letter, a number, a sign, and a logo.
122. The process according to embodiment 120 or embodiment 121, wherein the maximal compression force applied is about 1-40 kN.
123. The process according to any one of embodiments 120-122, wherein the so-formed tablet has a tablet porosity of between about 0-30% such as between about 5-25% such as between about 8-18%.
124. A punch set comprising an upper punch, a lower punch, and a die for making a tablet according to any one of embodiments 1-111.
125. The punches according to embodiment 124, wherein the punches have a single tip or multiple tips.
126. The punch set according to embodiment 124 or embodiment 125, wherein the die is tapered.
127. The punch set according to any one of embodiments 124-126, wherein the die is non-tapered.
128. The tablet according to any one of embodiments 53-61, wherein
   (a) the height to width ratio is about 0.7;
   (b) the tablet height to cup depth ratio is about 4.8;
   (c) the minor major radius to width ratio of about 1.48 and/or
   (d) the index value is about 0.38.
129. The tablet according to any one of embodiments 53-61, wherein
   (a) the height to width ratio is about 0.8;
   (b) the tablet height to cup depth ratio is about 5.1;
   (c) the minor major radius to width ratio of about 1.54 and/or
   (d) the index value is about 0.41.
130. The tablet according to any one of embodiments 43-52, wherein
   (a) the height to width ratio is about 0.8;
   (b) the tablet height to cup depth ratio is about 4.5;
   (c) the minor major radius to width ratio of about 1.77 and/or
   (d) the index value is about 0.54.
131. The tablet according to any one of embodiments 63-72, wherein
   (a) the height to width ratio is about 0.6;
   (b) the tablet height to cup depth ratio is about 5.0;
   (c) the minor major radius to width ratio of about 1.75 and/or
   (d) the index value is about 0.41.
132. The tablet according to any one of embodiments 73-84, wherein
   (a) the height to width ratio is about 0.8;
   (b) the tablet height to cup depth ratio is about 6.4;
   (c) the minor major radius to width ratio of about 1.75 and/or
   (d) the index value is about 0.41.
133. The tablet according to any one of embodiments 73-84, wherein
   (a) the height to width ratio is about 0.8;
   (b) the tablet height to cup depth ratio is about 5.6;
   (c) the minor major radius to width ratio of about 1.75 and/or
   (d) the index value is about 0.46.

METHODS AND EXAMPLES

List of Abbreviations

SNAC sodium N-(8-(2-hydroxybenzoyl)amino)caprylate
MgSt magnesium stearate

General Methods and Materials

Materials

Semaglutide can be prepared according to the method described in WO 2006/097537, Example 4. SNAC can be prepared according to the method described in WO 2008/028859.

Method 1: Tablet Preparation

Step 1: Granulation

The components (e.g. SNAC, MgSt and optionally semaglutide) were mixed at 25 rpm for 50 min using a diffusion blender prior to dry granulation. Dry granulation was carried out by roller compaction on a Gerteis Minipactor using a roll speed of 3-6 rpm, compaction forces of 6-9 kN/cm, and a gap of 1-2 mm. After roller compaction, comminution of the moldings into granules was carried out using a 0.80 mm screen. The so obtained granulated compositions (shown in Table 1) had median particle sizes of 256 to 402 μm and were then formed into tablets.

TABLE 1

Overview of components in compositions 1 to 8.

| | SNAC [mg] | MgSt [mg] | Semaglutide [mg] |
|---|---|---|---|
| Composition 1 | 300 | 7.7 | — |
| Composition 2 | 300 | 7.7 | 1 |
| Composition 3 | 100 | 2.6 | — |
| Composition 4 | 597.2 | 15.3 | — |
| Composition 5 | 397.3 | 10.2 | — |
| Composition 6 | 731.2 | 18.8 | — |
| Composition 7 | 975 | 25 | — |
| Composition 8 | 500 | 12.8 | — |

Step 2: Tabletting

Tablets were produced on a Fette 102*i* rotary press mounted with one or more sets of punches and dies and using a die table rotational speed of 20-50 rpm. The fill volume was adjusted to obtain the target weights of the tablets using a force feeder rotating at 20 rpm. The tablets were then compressed at pre-compression forces from 0 to 5 kN and main compression forces from 5 to 17 kN.

Method 2: Friability

Friability testing was performed according to section 2.9.7 in the European Pharmacopoeia 7.5, 7th edition 2012.

Figure 9:
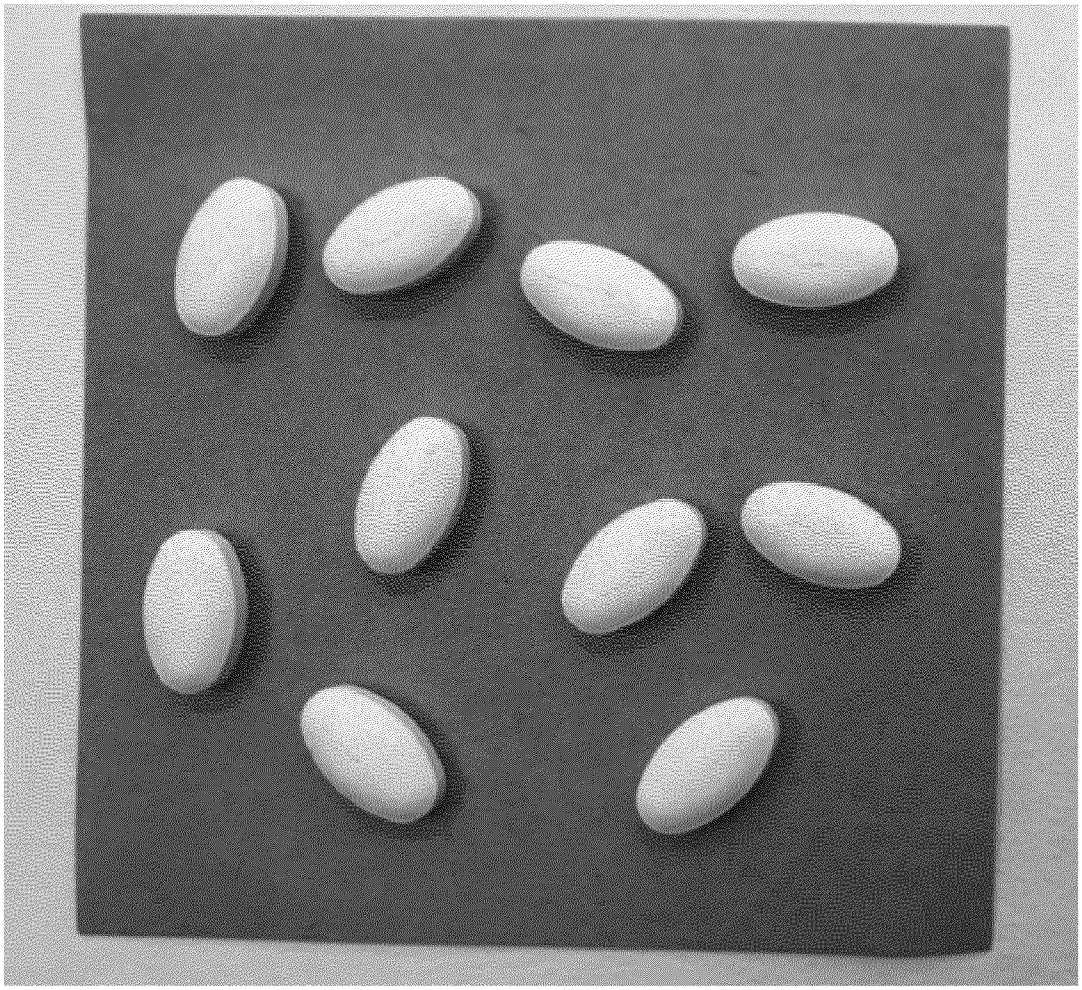
FIG. 9 shows exemplary tablets having one or more cracks.
Figure 10:
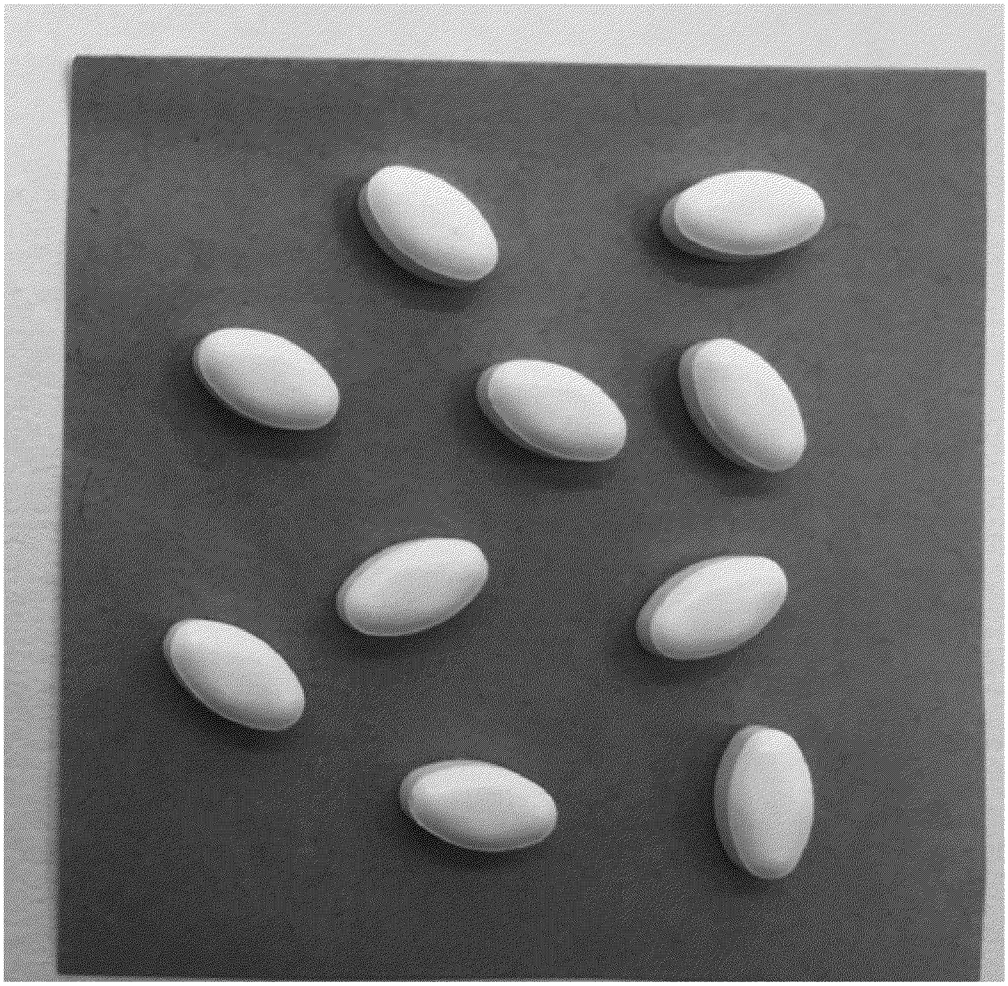
FIG. 10 shows exemplary tablets without cracks.
Figure 11:
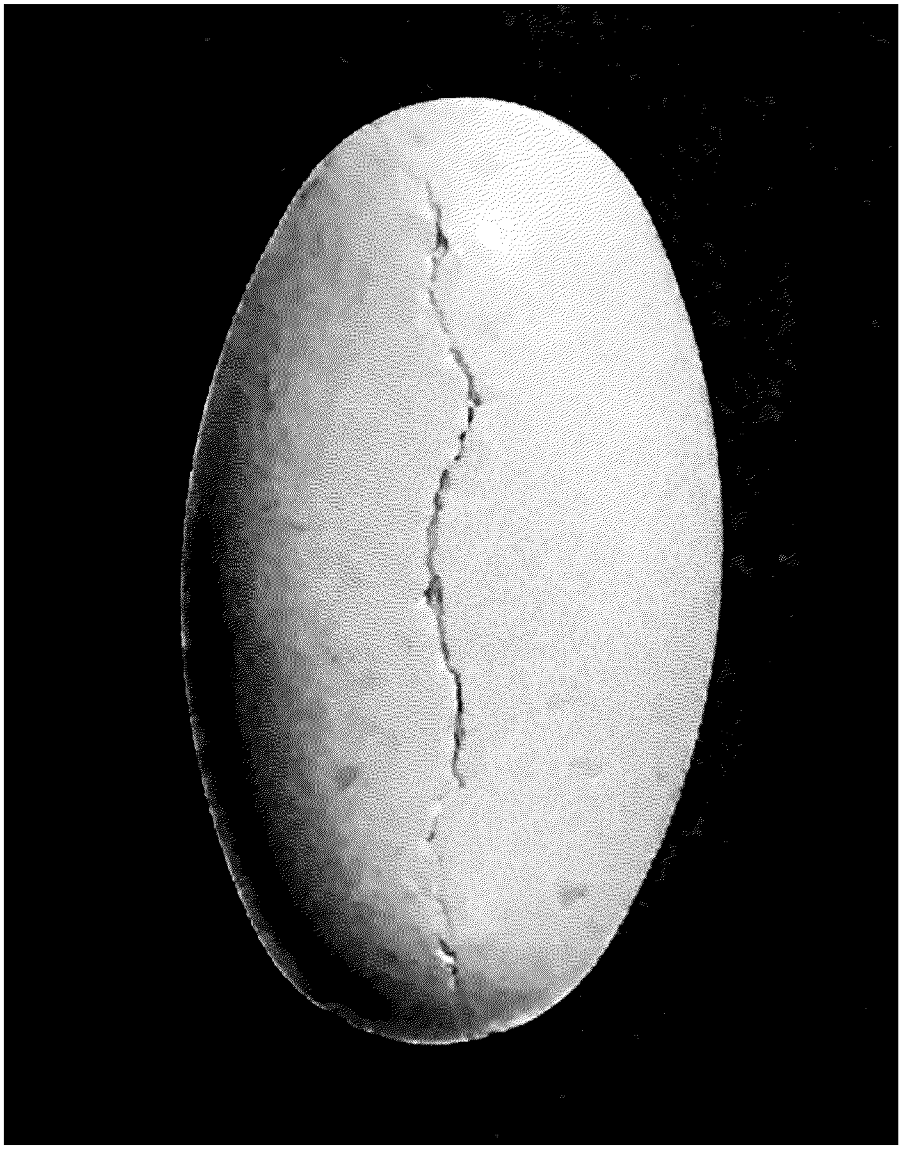
FIG. 11 shows an example of a tablet having a severe crack.

Method 3: Visual Evaluation 70 to 250 tablets were visually inspected for cracks in front of a well-lit white or coloured background. The tablets were visually inspected on one side and hereafter inspected on the other side. The number of tablets detected with cracks were counted and divided by the total number of tablets inspected and reported as a percentage. An example of tablets having cracks is shown in FIG. 9. An example of tablets without cracks is shown in FIG. 10. An example of a tablet with a severe crack is shown in FIG. 11.

Method 4: Median Particle Size

The median particle size, i.e. the volume distribution of equivalent spherical diameters of particles, was determined by laser diffraction in the dry mode with a dispersive pressure of 1 barg and at an obscuration below 20% in a Malvern Mastersizer 3000 instrument using the non-spherical particle mode in general purpose (Mie approximation) and with a refractive index of 1.55.

Tablet Design

Tablet punch sets with the desired tablet designs were manufactured based on the tablet design drawings, prepared in the TabletCAD, tablet design program from Natoli Engineering Company, Inc. (https://natoli.com/lp/tabletcad-ddo/).

EXAMPLES

Example 1—Tablet Design

Tablet Design A-C

Three tablet designs (A-C) were prepared using TabletCAD. The parameters selected are shown in table 2. Composition 1 was used to prepare the tablets according to the procedure described in method 1.

The objective of this example was to determine the effect of tablet dimensions on the formation of cracks and on the tablet friability.

As can be seen from the results shown in Table 2, decreasing the length and width increases the total height of the tablet and leads to an increased percentage of tablets without cracks. In addition, increasing the cup depth decreases the percentage of tablets without cracks. Tablet friability of all tablets designs was found acceptable.

In conclusion, to decrease the number of tablets having cracks it is desirable that the total height of the tablet is as high as possible, while the cup depth remains as shallow as possible.

Tablet Designs D1-D2

Four tablet designs (D1-D4) were prepared using TabletCAD. The parameters selected are shown in Table 2. Composition 1 was used to prepare the tablets according to the procedure described in method 1.

The objective of this example was to specifically determine the effect of the minor minor cup radius on the formation of cracks and on the tablet friability.

As can be seen from the results in Table 2, the total tablet height between the tablets are found comparable, as expected with fixed tablet width and length. With the comparable total tablet height and identical cup depth, the results show that decreasing the minor minor radius increases the percentage of tablets without cracks. Tablet friability of all tablets designs was found acceptable.

In conclusion, to decrease the number of tablets having cracks it is desirable that the minor minor radius is as small as possible.

Tablet Designs E1-E2

Two tablet designs (E1-E2) were prepared using TabletCAD. The parameters selected are shown in table 2. Composition 2 was used to prepare the tablets according to the procedure described in method 1.

The objective of this example was to specifically determine the effect of cup depth on the formation of cracks and on the tablet friability.

As can be seen from the results in Table 2, the reduced cup depth for E2 slightly decreases the total tablet height, however, the tablets are found comparable with the only significant factor varied being the cup depth. The results show that decreasing the cup depth increases the percentage of tablets without cracks. However, a too shallow cup negatively affects the friability of the tablets.

In conclusion, to decrease the number of tablets having cracks it is desirable that the cup depth is as small as possible, yet deep enough to prevent undesirable tablet friability.

TABLE 2

Overview of tablet designs A-C, D1-D4, E1-E2.

| | A | B | C | D1 | D2 | D3 | D4 | E1 | E2 |
|---|---|---|---|---|---|---|---|---|---|
| Height 13 [mm] | 4.77 | 5.12 | 5.56 | 5.43 | 5.37 | 5.29 | 5.27 | 5.31 | 4.97 |
| Cup depth 11 [mm] | 1.25 | 1.2 | 1.15 | 1.1 | 1.1 | 1.1 | 1.1 | 1.1 | 0.7 |
| Core height 7 [mm] | 2.27 | 2.72 | 3.26 | 3.23 | 3.17 | 3.09 | 3.07 | 3.11 | 3.57 |

TABLE 2-continued

Overview of tablet designs A-C, D1-D4, E1-E2.

| | A | B | C | D1 | D2 | D3 | D4 | E1 | E2 |
|---|---|---|---|---|---|---|---|---|---|
| Major axis 3 [mm] | 13 | 12.5 | 12 | 12 | 12 | 12 | 12 | 12 | 12 |
| Minor axis 4 [mm] | 7.5 | 7 | 6.5 | 6.8 | 6.8 | 6.8 | 6.8 | 6.8 | 6.8 |
| Major major radius 9 [mm] | 35 | 35 | 35 | 35 | 35 | 35 | 35 | 35 | 35 |
| Major minor radius 10 [mm] | 4 | 4 | 4 | 4 | 4 | 4 | 4 | 3.2 | 3.2 |
| Minor major radius 14 [mm] | 10 | 10 | 10 | 12 | 12 | 12 | 12 | 12 | 12 |
| Minor minor radius 15 [mm] | 3 | 3 | 3 | 4.8 | 4.0 | 3.5 | 2.7 | 2.5 | 2.5 |
| Side radius 6 [mm] | 10.4 | 10 | 9.6 | 9.38 | 9.38 | 9.38 | 9.38 | 9.38 | 9.38 |
| End radius 5 [mm] | 2.78 | 2.49 | 2.2 | 2.4 | 2.4 | 2.4 | 2.4 | 2.4 | 2.4 |
| Index value (formula III) | 0.49 | 0.55 | 0.62 | 0.88 | 0.74 | 0.66 | 0.54 | 0.51 | 0.33 |
| Ratio (height/width) (formula VI) | 0.6 | 0.7 | 0.9 | 0.8 | 0.8 | 0.8 | 0.8 | 0.8 | 0.7 |
| Ratio (major axis/minor axis) (formula II) | 1.7 | 1.8 | 1.8 | 1.8 | 1.8 | 1.8 | 1.8 | 1.8 | 1.8 |
| Ratio (height/cup) (formula IV) | 3.8 | 4.3 | 4.8 | 4.9 | 4.9 | 4.8 | 4.8 | 4.8 | 7.1 |
| Ratio (minor major radius/width) (formula V) | 1.33 | 1.43 | 1.54 | 1.76 | 1.76 | 1.76 | 1.76 | 1.76 | 1.76 |
| Tablet porosity [%][1] | 16 | 15 | 14 | 16 | 15 | 14 | 14 | 15 | 14 |
| Tablet density [g/ml] | 1.07 | 1.09 | 1.10 | 1.08 | 1.09 | 1.10 | 1.10 | 1.09 | 1.10 |
| Tablet chipping during friability | none | none | none | none | none | none | none | none | unacceptable |
| Percentage of tablets without cracks [%] | 7 | 21 | 65 | 8 | 25 | 53 | 74 | 78 | 100 |

[1]Tablet porosity is calculated based on the maximum tablet density at 1.28 g/mL.

Based on the foregoing it can be concluded that length, width, total height, cup depth, minor major radius, cup width and minor minor radius are parameters that have an effect on the formation of cracks. In particular, it can be concluded that (a) a tablet height to width ratio of 0.9 or below, (b) a tablet height to cup depth ratio of above 4.3;

(c) a minor major radius to width ratio of above 1.15; and/or (d) an index value of 0.67 or below, lead to a decrease in tablets having cracks.

Example 2—Effect of Main Compression Force and Die Rotational Speed

Tablets based on the tablet designs of Example 1 were produced according to the tabletting procedure described in method 1 using the same compositions 1 and 2 as in Example 1, respectively.

The objective of this example was to determine if increased compression forces and lower die rotational speed could decrease the number of tablets having cracks compared to example 1.

As can be seen from the results in Table 3, decreasing the die rotational speed and increasing the compression force increases in general the number of tablets without cracks. However, the effect of die rotational speed on the increased number of tablets without cracks is found higher than compared to the effect of increased compression force. The effect of decreasing the die rotational speed and increasing the compression force is found insufficient to solve the issue with tablet cracks.

In conclusion, the modifications to the tablet design are required to obtain tablets without cracks as decreasing die rotational speed and increasing compression force are insufficient to prevent tablet cracks and as slower rotational speeds reduces the manufacturing through-put.

TABLE 3

Results of the visual evaluation of cracks on tablets based on tablet designs A-E compressed at various compression forces and die rotational speed.

| | A | | B | | C | | D1 | | D2 | | D3 | | D4 | | E1 | | E2 | |
|---|---|---|---|---|---|---|---|---|---|---|---|---|---|---|---|---|---|---|
| Compression force [kN] | 9 | 15 | 9 | 15 | 9 | 15 | 9 | 15 | 9 | 15 | 9 | 15 | 9 | 15 | 9 | 14 | 9 | 15 |
| Die rotational speed [rpm] | 50 | 20 | 50 | 20 | 50 | 20 | 50 | 20 | 50 | 20 | 50 | 20 | 50 | 20 | 50 | | 50 | |
| Percentage of tablets without cracks [%] | 7 | 20 | 21 | 18 | 65 | 100 | 8 | 45 | 25 | 55 | 53 | 78 | 74 | 100 | 78 | 66 | 100 | 100 |

Example 3—Effect of Tablet Weight

Based on the identified parameters in Examples 1 and 2, further tablet designs were prepared using TabletCAD. Designs F, G, and H were prepared with compositions 3, 1, and 4, respectively, and the tablets were prepared according to the procedure described in method 1. The parameters for the tablet designs F-H are shown in Table 4.

The objective of this example was to verify the design requirements set forth in example 1 for a variety of tablet weights ranging from 102.6 to 612.5 mg with respect to obtaining a high number of tablets without cracks.

As can be seen from the results in Table 4, the two optimised tablet designs complying with the design requirements set forth in example 1 (F and H) result in higher number of tablets without cracks whereas the tablet design not complying (G) has a reduced number of tablets without cracks. The results show therefore that the design requirements set forth in example 1 for obtaining high number of tablets without cracks are equally valid for other tablet weights.

TABLE 4

Overview of tablet designs F-H.

| | F | G | H |
|---|---|---|---|
| Tablet weight [mg] | 102.6 | 307.7 | 612.5 |
| Height 13 [mm] | 3.33 | 4.6 | 5.5 |
| Cup depth 11 [mm] | 0.74 | 1.15 | 1.15 |
| Core height 7 [mm] | 1.85 | 2.3 | 3.2 |
| Major axis 3 [mm] | 8.5 | 12.9 | 16.1 |
| Minor axis 4 [mm] | 5 | 7.3 | 9.1 |
| Major major radius 9 [mm] | 18 | 37.6 | 60 |
| Major minor radius 10 [mm] | 4 | 3.4 | 2.8 |
| Minor major radius 14 [mm] | 7 | 12.9 | 20 |
| Minor minor radius 15 [mm] | 3 | 2.7 | 2.5 |
| Side radius 6 [mm] | 6.222 | 10.183 | 13.883 |
| End radius 5 [mm] | 1.724 | 2.6 | 3.5 |
| Index value (formula III) | 0.67 | 0.5 | 0.37 |
| Ratio (height/width) (formula VI) | 0.7 | 0.6 | 0.6 |
| Ratio (major axis/minor axis) (formula II) | 1.7 | 1.8 | 1.8 |
| Ratio (height/cup) (formula IV) | 4.5 | 4.0 | 4.8 |
| Ratio (minor major radius/width) (formula V) | 1.40 | 1.77 | 2.20 |
| Tablet porosity [%][1] | 8 | 13 | 14 |
| Tablet density [g/ml] | 1.18 | 1.12 | 1.10 |
| Compression force [kN] | 5 | 9.5 | 15 |
| Die rotational speed [rpm] | 20 | 20 | 20 |
| Percentage of tablets without cracks [%] | 100 | 67 | 99 |

[1]Tablet porosity is calculated based on the maximum tablet density at 1.28 g/mL.

Further tablet designs (I-K) were prepared using TabletCAD for tablet weights ranging from 307.7-1000 mg (Table 5). Design I was prepared with compositions 1 and 5, design J was prepared with compositions 6 and 7 and design K was also prepared with compositions 6 and 7. The tablets were prepared according to the procedure described in method 1 and the parameters for the tablet designs I-K with low and high tablet weights are shown in Table 5.

The objective of this example was to verify the design requirements set forth in example 1 by reducing the ratio of the height to cup as calculated by formula IV within the same tablet design by lowering the tablet weight with respect to obtaining fewer number of tablets without cracks.

As can be seen from the results in Table 5, the optimised tablet designs complying with the design requirements set forth in example 1 (I—high, J—high and K—high) results in higher number of tablets without cracks whereas the tablet designs not complying (I—low, J—low and K—low) have a reduced number of tablets without cracks. The results show therefore that the design requirements set forth in example 1 for obtaining high number of tablets without cracks are equally valid for a range of tablet weights within a tablet design.

TABLE 5

Overview of tablet design G-K.

| | I - low | I - high | J - low | J - high | K - low | K - high |
|---|---|---|---|---|---|---|
| Tablet weight [mg] | 307.7 | 407.5 | 750 | 1000 | 750 | 1000 |
| Height 13 [mm] | 4.71 | 5.9 | 6.25 | 7.98 | 6.18 | 8.08 |
| Cup depth 11 [mm] | 1.3 | 1.3 | 1.25 | 1.25 | 1.45 | 1.45 |
| Core height 7 [mm] | 2.11 | 3.3 | 3.75 | 5.48 | 3.28 | 5.18 |
| Major axis 3 [mm] | 12.9 | 12.9 | 17.1 | 17.1 | 17.1 | 17.1 |
| Minor axis 4 [mm] | 7.3 | 7.3 | 9.7 | 9.7 | 9.7 | 9.7 |
| Major major radius 9 [mm] | 50 | 50 | 50 | 50 | 70 | 70 |
| Major minor radius 10 [mm] | 2.5 | 2.5 | 4.5 | 4.5 | 3 | 3 |
| Minor major radius 14 [mm] | 12.9 | 12.9 | 17 | 17 | 17 | 17 |
| Minor minor radius 15 [mm] | 2.7 | 2.7 | 3.5 | 3.5 | 3.5 | 3.5 |
| Side radius 6 [mm] | 11.06 | 11.06 | 13.271 | 13.271 | 14.5 | 14.5 |
| End radius 5 [mm] | 2.8 | 2.8 | 3.4 | 3.4 | 3.7 | 3.7 |
| Index value (formula III) | 0.54 | 0.54 | 0.41 | 0.41 | 0.46 | 0.46 |
| Ratio (height/width) (formula VI) | 0.6 | 0.8 | 0.6 | 0.8 | 0.6 | 0.8 |
| Ratio (major axis/minor axis) (formula II) | 1.8 | 1.8 | 1.8 | 1.8 | 1.8 | 1.8 |
| Ratio (height/cup) (formula IV) | 3.6 | 4.5 | 5.0 | 6.4 | 4.3 | 5.6 |
| Ratio (minor major radius/width) (formula V) | 1.77 | 1.77 | 1.75 | 1.75 | 1.75 | 1.75 |

TABLE 5-continued

| Overview of tablet design G-K. | | | | | | |
|---|---|---|---|---|---|---|
| | I - low | I - high | J - low | J - high | K - low | K - high |
| Tablet porosity [%][1] | 16 | 15 | 15 | 14 | 14 | 16 |
| Tablet density [g/ml] | 1.07 | 1.08 | 1.09 | 1.09 | 1.10 | 1.07 |
| Compression force [kN] | 9.5 | 9.5 | 16.5 | 16.5 | 18 | 17 |
| Die rotational speed [rpm] | 20 | 20 | 20 | 20 | 20 | 20 |
| Percentage of tablets without cracks [%] | 49 | 100 | 100 | 100 | 57 | 100 |

[1]Tablet porosity is calculated based on the maximum tablet density at 1.28 g/mL.

Further tablet designs (L-O) were prepared using Tablet-CAD for a tablet weight about 512.8 mg (Table 6). Designs L-O were prepared with composition 8 and the tablets were prepared according to the procedure described in method 1. The parameters for the tablet designs L-O are shown in Table 6.

The objective of this example was to verify the design requirements set forth in example 1 for a tablet weight of about 512.8 mg with respect to obtaining high number of tablets without cracks.

As can be seen from the results in Table 6, the optimised tablet designs complying with the design requirements set forth in example 1 (N and O) results in higher number of tablets without cracks whereas the tablet designs not complying (L and M) have a reduced number of tablets without cracks. The results show therefore that the design requirements set forth in example 1 for obtaining high number of tablets without cracks are equally valid for larger tablet weights

TABLE 6

| Overview of tablet design L-O. | | | | |
|---|---|---|---|---|
| | L | M | N | O |
| Height 13 [mm] | 5.54 | 5.15 | 6.13 | 5.79 |
| Cup depth 11 [mm] | 1.3 | 1.4 | 1.2 | 1.2 |
| Core height 7 [mm] | 2.94 | 2.35 | 3.73 | 3.39 |
| Major axis 3 [mm] | 15.2 | 16.1 | 13.8 | 14.3 |
| Minor axis 4 [mm] | 8.6 | 9.1 | 7.8 | 8.1 |
| Major major radius 9 [mm] | 60 | 60 | 40 | 40 |
| Major minor radius 10 [mm] | 2.5 | 2.1 | 3 | 3 |
| Minor major radius 14 [mm] | 15 | 20 | 12 | 12 |
| Minor minor radius 15 [mm] | 2.5 | 2.5 | 2.5 | 2.5 |
| Side radius 6 [mm] | 14.4 | 15.26 | 10.99 | 10.99 |
| End radius 5 [mm] | 3.5 | 3.7 | 2.8 | 2.8 |
| Index value (formula III) | 0.40 | 0.41 | 0.41 | 0.38 |
| Ratio (height/width) (formula VI) | 0.6 | 0.6 | 0.8 | 0.7 |
| Ratio (major axis/minor axis) (formula II) | 1.8 | 1.8 | 1.8 | 1.8 |
| Ratio (height/cup) (formula IV) | 4.3 | 3.7 | 5.1 | 4.8 |
| Ratio (minor major radius/width) (formula V) | 1.74 | 2.20 | 1.54 | 1.48 |
| Tablet porosity [%][1] | 16 | 18 | 10 | 10 |
| Tablet density [g/ml] | 1.07 | 1.05 | 1.15 | 1.16 |
| Compression force [kN] | 17 | 17 | 17 | 17 |
| Die rotational speed [rpm] | 20 | 20 | 20 | 20 |
| Percentage of tablets without cracks [%] | Cracks | Cracks | No cracks | No cracks |

[1]Tablet porosity is calculated based on the maximum tablet density at 1.28 g/mL.

In conclusion, the tablet design requirements for preventing tablet cracks are verified for different tablet weights.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. An elongated oval-shaped compound cup tablet comprising sodium N-(8-(2-hydroxybenzoyl) amino) caprylate (SNAC) in a total amount of about 60 to 99.8% (w/w) and an active pharmaceutical ingredient (API) in an amount of 0.1-40% (w/w), the tablet further comprising (a) a tablet height to width ratio of 0.9 or below;

(b) a tablet height to cup depth ratio of above 4.3;

(c) a minor major radius to width ratio of above 1.15; and (d) an index value of 0.67 or below.

2. The tablet according to claim 1, wherein the SNAC is present in a total amount of about 75-99% in weight based on the total weight of the tablet.

3. The tablet according to claim 1, wherein the API is present in 0.1 to 14% (w/w).

4. The tablet according to claim 1, wherein the API is semaglutide.

5. The tablet according to claim 1, wherein the tablet further comprises a lubricant.

6. The tablet according to claim 5, wherein the lubricant is present in a total amount of about 0.1-7%, based on the total weight of the tablet.

7. The tablet according to claim 5, wherein the lubricant is magnesium stearate.

8. The tablet according to claim 1, wherein the tablet further comprises one or more pharmaceutically acceptable excipients.

9. The tablet according to claim 1, wherein the tablet essentially consists of 84-97% SNAC, 0.1-14% semaglutide and 1.5-3.5% magnesium stearate, based on the total weight of the tablet.

10. The tablet according to claim 1, wherein the total weight of the tablet is about 50 to 1200 mg.

11. The tablet according to claim 1, wherein the total weight of the tablet is in a range of about 290 to 390 mg.

12. The tablet according to claim 1, the tablet further comprising a) a major axis of about 10.0-14.0 mm;

b) a minor axis of about 5.1-8.5 mm;

c) a side radius of about 8.0-13.1 mm;

d) end radius of about 1.8-3.0 mm;

e) a cup depth of about 0.7 to 1.5 mm;

f) a major major radius of above 19.3 mm;

g) major minor radius of below 16.0 mm;

h) minor major radius of above 6.6 mm; and/or i) minor minor radius of below 5.0 mm.

13. The tablet according to claim 1, the tablet further comprising a) a major axis of about 11.7-16.5 mm;

b) a minor axis of about 6.0-10.0 mm;

c) a side radius of about 9.4-15.4 mm;

d) end radius of about 2.1-3.5 mm;

e) a cup depth of about 0.8-1.8 mm;

f) a major major radius of above 22.6 mm;

g) major minor radius of below 18.8 mm;

h) minor major radius of above 7.8 mm; and/or i) minor minor radius of below 5.9 mm.

14. A method of treating diabetes or obesity, comprising administering the tablet according to claim 1 to a patient in need thereof.

* * * * *